(12) United States Patent
Zijderveld et al.

(10) Patent No.: US 10,627,817 B2
(45) Date of Patent: Apr. 21, 2020

(54) VEHICLE MANIPULATION USING OCCUPANT IMAGE ANALYSIS

(71) Applicant: Affectiva, Inc., Boston, MA (US)

(72) Inventors: Gabriele Zijderveld, Somerville, MA (US); Rana el Kaliouby, Milton, MA (US); Abdelrahman N Mahmoud, Somerville, MA (US); Seyedmohammad Mavadati, Watertown, MA (US)

(73) Assignee: Affectiva, Inc., Boston, MA (US)

( * ) Notice: Subject to any disclaimer, the term of this patent is extended or adjusted under 35 U.S.C. 154(b) by 59 days.

(21) Appl. No.: 15/875,644

(22) Filed: Jan. 19, 2018

(65) Prior Publication Data

US 2018/0143635 A1   May 24, 2018

Related U.S. Application Data

(63) Continuation-in-part of application No. 15/273,765, filed on Sep. 23, 2016, which is a continuation-in-part of application No. 14/796,419, filed on Jul. 10, 2015, now abandoned, which is a continuation-in-part of application No. 14/460,915, filed on Aug. 15, 2014, and a continuation-in-part of application No. 13/153,745, filed on Jun. 6, 2011, now abandoned.

(Continued)

(51) Int. Cl.
*G05D 1/00* (2006.01)
*G06N 3/04* (2006.01)
(Continued)

(52) U.S. Cl.
CPC ......... *G05D 1/0088* (2013.01); *A61B 5/0013* (2013.01); *A61B 5/0077* (2013.01);
(Continued)

(58) Field of Classification Search
USPC ........................................................ 701/36
See application file for complete search history.

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Tyler D Paige
(74) *Attorney, Agent, or Firm* — Adams Intellex, PLC

(57) ABSTRACT

Vehicle manipulation is performed using occupant image analysis. A camera within a vehicle is used to collect cognitive state data including facial data, on an occupant of a vehicle. A cognitive state profile is learned, on a first computing device, for the occupant based on the cognitive state data. The cognitive state profile includes information on absolute time. The cognitive state profile includes information on trip duration time. Voice data is collected and the cognitive state data is augmented with the voice data. Further cognitive state data is captured, on a second computing device, on the occupant while the occupant is in a second vehicle. The further cognitive state data is compared, on a third computing device, with the cognitive state profile that was learned for the occupant. The second vehicle is manipulated based on the comparing of the further cognitive state data.

26 Claims, 16 Drawing Sheets

Related U.S. Application Data

(60) Provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | |
|---|---|
| *G08G 1/0967* | (2006.01) |
| *G10L 25/48* | (2013.01) |
| *A61B 5/00* | (2006.01) |
| *B60W 40/08* | (2012.01) |
| *G10L 15/18* | (2013.01) |
| *G10L 25/63* | (2013.01) |
| *G10L 15/22* | (2006.01) |
| *A61B 5/16* | (2006.01) |
| *A61B 5/18* | (2006.01) |
| *A61B 5/1171* | (2016.01) |
| *G05D 1/02* | (2020.01) |
| *G08G 1/0962* | (2006.01) |
| *G06K 9/00* | (2006.01) |
| *G08G 1/01* | (2006.01) |
| *G06K 9/62* | (2006.01) |
| *G06N 20/00* | (2019.01) |
| *G10L 25/90* | (2013.01) |

(52) U.S. Cl.
CPC ............ *A61B 5/1176* (2013.01); *A61B 5/165* (2013.01); *A61B 5/18* (2013.01); *A61B 5/4803* (2013.01); *A61B 5/6893* (2013.01); *B60W 40/08* (2013.01); *G05D 1/0221* (2013.01); *G05D 1/0291* (2013.01); *G06K 9/00315* (2013.01); *G06K 9/00845* (2013.01); *G06K 9/6273* (2013.01); *G06N 3/0454* (2013.01); *G06N 20/00* (2019.01); *G08G 1/0112* (2013.01); *G08G 1/0129* (2013.01); *G08G 1/0962* (2013.01); *G08G 1/096716* (2013.01); *G08G 1/096725* (2013.01); *G08G 1/096741* (2013.01); *G08G 1/096775* (2013.01); *G10L 15/1815* (2013.01); *G10L 15/22* (2013.01); *G10L 25/48* (2013.01); *G10L 25/63* (2013.01); *A61B 2576/02* (2013.01); *G10L 15/1807* (2013.01); *G10L 25/90* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |

(56) References Cited

U.S. PATENT DOCUMENTS

| | | |
|---|---|---|
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,738,523 B1* | 5/2014 | Sanchez ............ G06Q 40/00 705/39 |
| 8,947,217 B2 | 2/2015 | Moussa et al. |
| 9,104,537 B1* | 8/2015 | Penilla ................ G06F 17/00 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2003/0220550 A1* | 11/2003 | McCulloch .......... A61B 5/1455 600/323 |
| 2004/0036601 A1* | 2/2004 | Obradovich ........ B60C 23/0408 340/540 |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0027583 A1* | 2/2007 | Tamir ................ G06Q 30/0283 701/1 |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0027337 A1* | 1/2008 | Dugan ................ A61B 5/0002 600/508 |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0143872 A1* | 6/2010 | Lankteee ............ G09B 19/167 434/65 |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0083960 A1* | 4/2012 | Zhu ...................... G05D 1/0214 701/23 |
| 2012/0109452 A1 | 5/2012 | Autran et al. |
| 2012/0324491 A1 | 12/2012 | Bathiche et al. |
| 2013/0023337 A1 | 1/2013 | Bowers et al. |
| 2013/0116587 A1 | 5/2013 | Sornmo et al. |
| 2013/0197409 A1 | 8/2013 | Baxter et al. |
| 2013/0204455 A1* | 8/2013 | Chia ..................... G07C 5/008 701/1 |
| 2014/0171752 A1 | 6/2014 | Park et al. |
| 2014/0172910 A1 | 6/2014 | Jung et al. |
| 2014/0218187 A1* | 8/2014 | Chun .................... G08B 21/06 340/439 |

(56) References Cited

U.S. PATENT DOCUMENTS

| | | | | |
|---|---|---|---|---|
| 2014/0306799 A1* | 10/2014 | Ricci | ...................... | H04W 4/21 340/5.83 |
| 2014/0309790 A1* | 10/2014 | Ricci | ...................... | H04W 4/21 700/276 |
| 2015/0025917 A1* | 1/2015 | Stempora | ............... | G06Q 40/08 705/4 |
| 2015/0254955 A1* | 9/2015 | Fields | .................... | G08B 21/02 705/4 |
| 2015/0258995 A1 | 9/2015 | Essers et al. | | |
| 2016/0104486 A1 | 4/2016 | Penilla et al. | | |
| 2017/0003784 A1 | 1/2017 | Garg et al. | | |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

VEHICLE MANIPULATION USING OCCUPANT IMAGE ANALYSIS

RELATED APPLICATIONS

This application claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

This application is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The foregoing applications are each hereby incorporated by reference in their entirety.

FIELD OF INVENTION

This application relates generally to automotive and vehicular manipulation and more particularly to vehicle manipulation using occupant image analysis.

BACKGROUND

People undertake travel for a wide range of purposes. Travel, which usually involves moving one or more people from one location to another, can be undertaken for financial reasons such as commuting to and from work or school, for personal reasons such as pleasure, relaxation, or discovery, or for exercise, to name only a few. Travel can also result from more sinister events such as war, famine, or displacement. Depending on the purpose of the travel and the modes of transportation available, people choose a mode of transportation based on convenience, availability, or cost. The modes of transportation include ground transportation, water transportation, and air transportation. Ground transportation can be accomplished on foot, by animal, or by vehicle such as a bicycle, an automobile, a van, a bus, or a train. Water transportation can include using a personal vehicle such as a raft, canoe, or kayak, a public vehicle such as a ferry or a ship, among others. Air transportation can be accomplished using an airship or airplane. Whichever mode of transportation is chosen by a person, the mode most often involves a vehicle.

People spend a tremendous amount of time in vehicles. Whether waiting for a vehicle, traveling in the vehicle, attempting to park the vehicle, waiting in security lines to get on a vehicle, among many other travel-related activities, substantial portions of time are committed to vehicular travel. Typical vehicle-related travel events include the daily commute; taking the kids to athletics practices, musical instrument lessons, or debate club; taking the pets to the veterinary clinic; shopping for food or household items; traveling; or any of the other common activities that require transportation, people use a variety of vehicles to meet their transportation needs. Traveling in a vehicle is time consuming at best, and at worst, boring, frustrating, and irritating. Rush hour traffic, accidents, and poorly maintained roads, among other situations, further complicate automotive transportation. The difficulties of transportation are also compounded by operating an unfamiliar vehicle, traveling in an unfamiliar city, and even having to remember to drive on the opposite side of the road in a construction zone or when traveling in some foreign countries. Sadly, these transportation realities can have catastrophic consequences. Irritated operators of vehicles can experience road rage and other antisocial behaviors, and bored, sleepy, impaired, distracted, or otherwise inattentive drivers can cause vehicular accidents and injury to themselves, pedestrians, bicyclists, animals, and property.

SUMMARY

Vehicular manipulation uses occupant image analysis. The vehicle to be manipulated can be an autonomous vehicle, a semi-autonomous vehicle, and so on. An in-vehicle camera is used to collect cognitive state data from an occupant of the vehicle. The occupant can be the operator of the vehicle or a passenger in the vehicle. The cognitive state data can include image data, facial data, etc. Other in-vehicle sensors can include a microphone for collecting voice data or audio data, and other sensors to collect physiological data. The cognitive state data is collected from the operator or passenger of a vehicle. The vehicle can be a first vehicle, a second vehicle, a public transportation vehicle, etc. The image data and facial image data can be captured using one or more cameras or another image capture apparatus. One or more cognitive state profiles are learned for the occupant of the vehicle. The one or more cognitive state profiles are based on the cognitive state data that was obtained. The cognitive state profile can include cognitive states, mental states, emotional states, moods, preferences of the occupant, and so on. Further cognitive state data is captured from the occupant. The further cognitive state data can be collected while the occupant is in a second vehicle. The second vehicle can be the same vehicle, a second vehicle, a vehicle from a fleet of vehicles, and so on. The further cognitive state data is compared with the cognitive state profile that was generated for the occupant. The comparing of the further cognitive state data can include identifying the occupant of the second vehicle, determining any differences in cognitive state data collected within the vehicle with that cognitive state data collected within the second vehicle, and so on. The second vehicle is manipulated based on the comparing of the further cognitive state data. The manipulation of the second vehicle can be the same as the manipulation of a first vehicle, can be adapted to a specific make or class of the second vehicle, can be tailored to the second vehicle based on tires or other equipment, can be modified based on weather patterns, traffic patterns, and so on.

In embodiments, a computer-implemented method for vehicle manipulation comprises: collecting, using a camera within a vehicle, cognitive state data including facial data, on an occupant of a vehicle; learning, on a first computing device, a cognitive state profile for the occupant based on the cognitive state data; capturing, on a second computing device, further cognitive state data on the occupant while the occupant is in a second vehicle; comparing, on a third computing device, the further cognitive state data with the cognitive state profile that was learned for the occupant; and manipulating the second vehicle based on the comparing of the further cognitive state data. In some embodiments, the method includes collecting voice data and augmenting the cognitive state data with the voice data. The occupant can be a passenger within the vehicle. The vehicle can be an autonomous vehicle or a semi-autonomous vehicle. In embodiments, the method includes using the cognitive state profile across a fleet of vehicles. The manipulating can include locking out operation of the vehicle; recommending a break for the occupant; recommending a different route; recommending how far to drive; responding to traffic; adjusting seats, mirrors, climate control, lighting, music, audio stimuli, interior temperature for the second vehicle; brake activation; or steering control. In other embodiments, the manipulating can be based on a make for the second vehicle, a vehicle class for the second vehicle, tires for the second vehicle, a weather pattern, and a traffic pattern.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
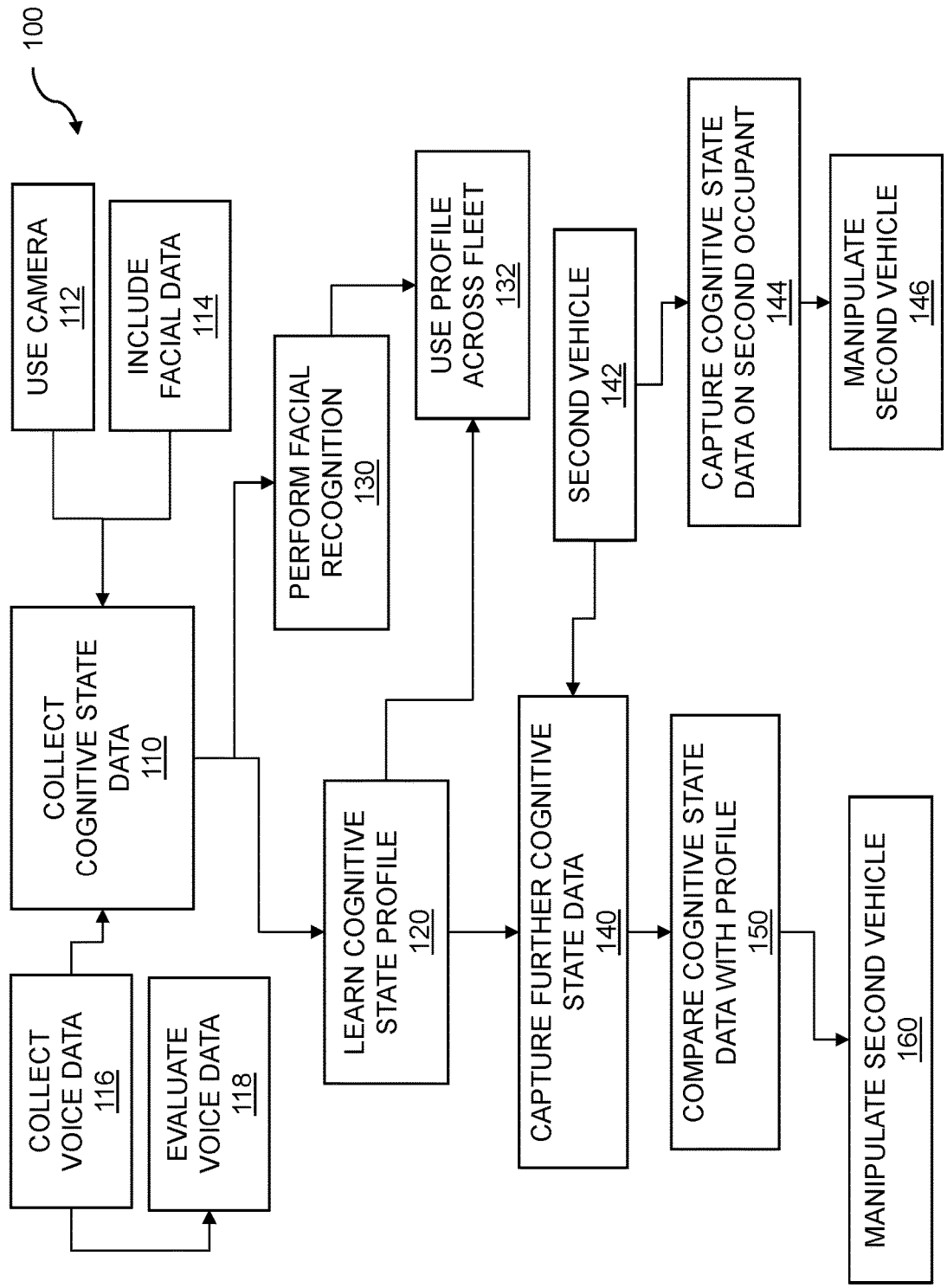
FIG. 1 is a flow diagram for vehicle manipulation using occupant image analysis.

Individuals can spend hundreds of hours or more per year traveling in vehicles such as buses, trains, airplanes, automobiles, and so on. The hours in vehicles are spent commuting, running errands, traveling, and so on. In vehicles where the vehicle occupant is not primarily concerned with operating the vehicle, such as a train or self-driving (autonomous) automobile, the hours can be spent enjoying entertainment options within the vehicle. Movies, games, video and/or phone calls, and the like are all options. Furthermore, entertainment option choices can be influenced by the vehicle ride experience and vice versa. For example, for some occupants, a high-traffic ride scenario with stop-and-go traffic may be a distracting influence for watching a serious, intense movie. Alternatively, for other occupants, a serious, intense movie may be just what is needed to take the occupant's mind off of an otherwise nerve-wracking experience. An occupant's cognitive state data can be a critical element for optimizing vehicle operation and vehicle entertainment experiences. This is especially critical for travel in autonomous or partially- or semi-autonomous vehicles.

While an individual is traveling within or atop a vehicle, that individual can present a wide variety of cognitive state data. The cognitive state data can include facial data, image data, voice data, audio data, physiological data, and so on. A cognitive state profile can be learned from the collected cognitive state data. The cognitive state profile can be used to identify an occupant of a vehicle, to determine the cognitive state of the individual, and so on. The identification of the occupant can be used for validation or verification purposes, for configuring the vehicle, and the like. The vehicle can be an autonomous vehicle or a semi-autonomous vehicle. The assessment of the cognitive state of the individual can be used to determine whether the occupant should operate the vehicle, take a break from traveling in the vehicle, seek an alternative travel route, etc. By doing so, road safety can be improved, and the transportation experience of the occupant or occupants in the given vehicle can be improved. Collecting cognitive state data and learning cognitive state profiles about the vehicle operator or passenger enables adaptation of both vehicle operating characteristics and vehicle environmental experiences for the operators and passengers.

Cognitive state data can be collected from an individual, where the cognitive state data can include facial data, voice data, physiological data, and so on. The cognitive state data of the individual can be used to understand other states of the individual such as emotional states, mental states, moods, and so on. Cognitive state data can be collected from an individual in order to learn a cognitive state profile the individual. The cognitive state profile can include information relating to the individual such as preferences for vehicle type, choices for settings and adjustments within the vehicle, and so on. By learning the cognitive state profile of the individual, further data can be collected and compared to the cognitive state profile. The comparing can be the basis for manipulating a second vehicle. The vehicle or vehicles that can be manipulated can include autonomous vehicles or semi-autonomous vehicles. The benefits of manipulating an autonomous vehicle or a semi-autonomous vehicle include: reducing the time required to configure a vehicle to an individual; verifying that the individual is in a cognitive state capable of operating the vehicle, that the individual is permitted to operate the vehicle, etc.; enhancing the transportation experience for the individual; and improving road safety. The enhanced transportation experience for the individual includes autonomous operation, security, or comfort. The road safety improvements derive from aiding the individual who is navigating in foreign surroundings or operating an unfamiliar vehicle, and from preventing a sleepy, impaired, or inattentive individual from operating the vehicle.

In the disclosed techniques, vehicles including semi-autonomous vehicles and autonomous vehicles can be manipulated. The manipulation of the vehicles can be performed for a variety of purposes including assisting an occupant of the vehicle, choosing routes for the vehicle, improving comfort of the occupant, reducing stress and other negative cognitive states, and so on. The vehicle manipulation uses occupant image analysis. A camera within the vehicle is used for collecting cognitive state data, including facial data, on an occupant of a vehicle. The camera can include a video camera, a still camera, a camera array, a plenoptic camera, a web-enabled camera, a near infrared camera, an RGB camera, and so on. A cognitive state profile for the occupant can be developed based on the cognitive state data. The cognitive state profile can include information on absolute time, where absolute time can include time of day, day of week, day of month, time of year information, and so on. Further cognitive state data on the occupant is captured while the occupant is in a second vehicle. The second vehicle can be the same vehicle, can be a different vehicle from a fleet of vehicles, or can be a different vehicle based on make and class. The cognitive data can be based on weather pattern or traffic pattern, and so on. The further cognitive state data is compared with the cognitive state profile that was developed for the occupant. The comparing of the further cognitive state data with the cognitive state profile can identify differences as the occupant of the second vehicle interacts with the second vehicle. The difference can include differences in cognitive states. The cognitive state data can be used in the detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The second vehicle is manipulated based on the comparing of the further cognitive state data. The manipulating of the second vehicle can include a locking out operation; recommending a break for the occupant; recommending a different route; recommending how far to drive; responding to traffic; adjusting seats, mirrors, climate control, lighting, music, audio stimuli, interior temperature for the second vehicle; brake activation; steering control; and so on. The manipulating of the second vehicle can be based on a make for the second vehicle, a vehicle class for the second vehicle, tires for the second vehicle, a weather pattern, and a traffic pattern.

FIG. 1 is a flow diagram for vehicle manipulation using occupant image analysis. A cognitive state profile is learned for an individual based on collected cognitive state data. Further data is collected and compared to the cognitive state profile. The comparing is used for manipulating a vehicle. A camera within a vehicle is used for collecting cognitive state data including facial data on an occupant of a vehicle. A cognitive state profile is developed for the occupant based on the cognitive state data. Further cognitive state data on the occupant is captured while the occupant is in a second vehicle. The further cognitive state data is compared with the cognitive state profile that was learned for the occupant. The second vehicle is manipulated based on the comparing of the further cognitive state data. In some embodiments, manipulation can simply include monitoring an occupant or driver within a vehicle. The flow 100 includes collecting cognitive state data 110. The cognitive state data can be collected using a camera 112 within a vehicle and can comprise images of the occupant. The cognitive state data can include facial data 114 on an occupant of a vehicle using the images of the occupant. The camera can be coupled to an electronic device, a vehicle, etc., with which the one or more people are interacting. More than one camera can be used for the obtaining of a series of images. The camera or cameras can include a webcam, where a webcam can include a video camera, a still camera, a thermal imager, a CCD device, a phone camera, a three-dimensional camera, a depth camera, a plenoptic camera, multiple webcams used to show different views of a person, or any other type of image capture apparatus that can allow captured data to be analyzed in an electronic system. The camera can be used to capture image data, where the image data includes the occupant of the vehicle. The image data can include other occupants of the vehicle. In embodiments, the occupant can be a passenger within the vehicle. The image data can include facial data, where the facial data includes the face of the occupant of the vehicle. In embodiments, the manipulating the vehicle can include capturing cognitive state data on a second occupant and can include manipulating a vehicle based on the cognitive state data for the occupant and the cognitive state data for the second occupant.

The flow 100 can include collecting voice data 116 and augmenting the cognitive state data with the voice data. The collecting voice data can include using a microphone, an audio transducer, or other type of audio capture apparatus that can permit using captured audio data such as voice data to be used in an electronic system. The voice data can include audio data, where the audio data can include ambient noise such as road noise, interior sound such as an audio source selected by the occupant, and so on. In some embodiments, cognitive state data simply includes audio and voice data without facial data. In some embodiments, audio data is evaluated based on expected interior or exterior noise for the vehicle. Noise cancellation can be performed. The various occupants of a vehicle can be identified and their voices can be localized for further analysis. The vehicle manipulation then can be based on this audio cognitive state data alone. In other embodiments, the audio cognitive state data can be combined with other types of cognitive state data. Various modalities of cognitive state data can be combined. In some embodiments, the augmenting can be based on lexical analysis of the voice data that evaluates sentiment. Sentiment can include affective states, subjective information, and so on. Sentiment can be analyzed to determine a vehicle operator's attitude toward a vehicle, travel, travel conditions, etc. The lexical analysis can be used to determine cognitive state, mental state, emotional state, mood, and so on. The cognitive state data and the augmenting voice data can be used in detection of one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In embodiments, the voice data can include non-speech vocalizations. The non-speech vocalizations can include sounds produced by the occupant of the vehicle. In embodiments, the non-speech vocalizations include grunts, yelps, squeals, snoring, sighs, laughter, filled pauses, unfilled pauses, or yawns. The flow 100 includes evaluating the voice data 118 for timbre, prosody, vocal register, vocal resonance, pitch, loudness, speech rate, or language content. The evaluating the voice data can be included in determining a cognitive state for an occupant of the vehicle. The voice data that is captured can be converted to text and the text can be analyzed.

The flow 100 includes learning, on a first computing device, a cognitive state profile 120 for the occupant based on the cognitive state data. In embodiments, an identity is recognized for the occupant. The identity can be recognized based on facial recognition, voice print recognition, userid entry, mobile phone recognition, key fob recognition, or by recognition of some other electronic signature. The cognitive state profile can include information relating to the occupant of the vehicle including schedules, preferences, a user identification (ID), and so on. The cognitive state profile can include information on trip duration time. The trip duration time can include information on typical time, expected time, increased time due to traffic conditions and weather conditions, and so on. In embodiments, the profile can include information on absolute time. The absolute time information included in the cognitive state profile can be used for determining whether travel conditions such as rush hour conditions can complicate travel for the occupant and whether the occupant may prefer a warmer or cooler environment in the vehicle, calming classical music instead of invigorating heavy metal selections, and so on. The absolute time can include time of day, day of week, day of month, or time of year information. The flow 100 includes performing facial recognition 130 on the occupant. Facial recognition on the occupant can include using classifiers. The classifiers can be used along with weights by a deep neural network. Facial recognition on the occupant can be based on identifying facial landmarks, facial regions, distinguishing facial characteristics such as scars, moles, facial hair, facial jewelry, etc. Based on the facial recognition, embodiments include using the cognitive state profile across a fleet 132 of vehicles. The using the cognitive state profile and the facial recognition of the occupant can be used for vehicle manipulation across the fleet of vehicles. In embodiments, the cognitive state profile is based on cognitive state event temporal signatures. The temporal signatures, which can include rise time, duration, fall time, etc., can be used to determine a duration of a cognitive state, an intensity of a cognitive state, and so on.

The flow 100 includes capturing further cognitive state data 140 on the occupant while the occupant is in a second vehicle 142. The capturing of further cognitive state data on the occupant can be used to enhance the learned cognitive state profile, to identify the occupant, and so on. The second vehicle 142 can be any of a variety of vehicles including automobiles, trucks, buses, sport utility vehicles (SUV), specialty vehicles, motorcycles, scooters, mopeds, bicycles, boats, and so on. In embodiments, the vehicle which can be manipulated and the second vehicle are a same vehicle. As previously discussed, the cognitive state data can be collected at all times of day, on different days, in different seasons, and so on. In embodiments, the vehicle and the second vehicle can be different vehicles. In other embodiments, the vehicle and the second vehicle can be part of a fleet of vehicles. The one or more of the vehicle, the second vehicle, and the fleet of vehicles can all be autonomous or semi-autonomous vehicles, and so on. As mentioned above, the flow 100 includes capturing cognitive state data on a second occupant 144 and manipulating the second vehicle 146 based on the cognitive state data for the occupant and the cognitive state data for the second occupant. The captured cognitive state data from the second occupant can be used for selecting a route based on preferences of the occupant and the second occupant, choosing mutually agreeable music, controlling climate zones within the vehicle, and so on.

The flow 100 includes comparing, on a third computing device, the further cognitive state data with the cognitive state profile 150 that was learned for the occupant. In embodiments, the second computing device and the third computing device can be the same device. The further cognitive state data can include facial data, voice data, audio data, physiological data, and so on. As stated throughout, the comparing of the further cognitive state data with the cognitive state profile can be used to identify an occupant, to improve a cognitive state profile for the occupant, to identify a cognitive state for the occupant such as sadness, stress, happiness, mirth, etc., and so on. In embodiments, the occupant whose cognitive state data is captured can be a passenger within the vehicle. There can be more than one passenger in the vehicle. The vehicle can be an autonomous vehicle such as a self-driving automobile, an autonomous truck, and so on. In embodiments, the vehicle can be a semi-autonomous vehicle. The semi-autonomous vehicles can include self-parking cars, collision avoidance signals such as alarms and haptic indications such as shaking seats, and so on.

The flow 100 includes manipulating the second vehicle 160 based on the comparing of the further cognitive state data. The manipulating the second vehicle can include setting up the second vehicle for the occupant who can be identified or whose cognitive state profile is loaded, operating the vehicle in a manner appropriate to or preferred by the occupant and so on. In embodiments, the manipulating includes a locking out operation; recommending a break for the occupant; recommending a different route; recommending how far to drive; responding to traffic; adjusting seats, mirrors, climate control, lighting, music, audio stimuli, interior temperature for the second vehicle; brake activation; or steering control. These manipulations of the vehicle can be performed for the safety, convenience, comfort, etc., of the one or more occupants of the vehicle. In other embodiments, the manipulating is based on a make for the second vehicle, a vehicle class for the second vehicle, tires for the second vehicle, a weather pattern, and a traffic pattern. Changes can be made to the manipulation of the second vehicle based on equipment options and features of the second vehicle. Routes can be selected based on tires, suspension, steering stability, etc. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
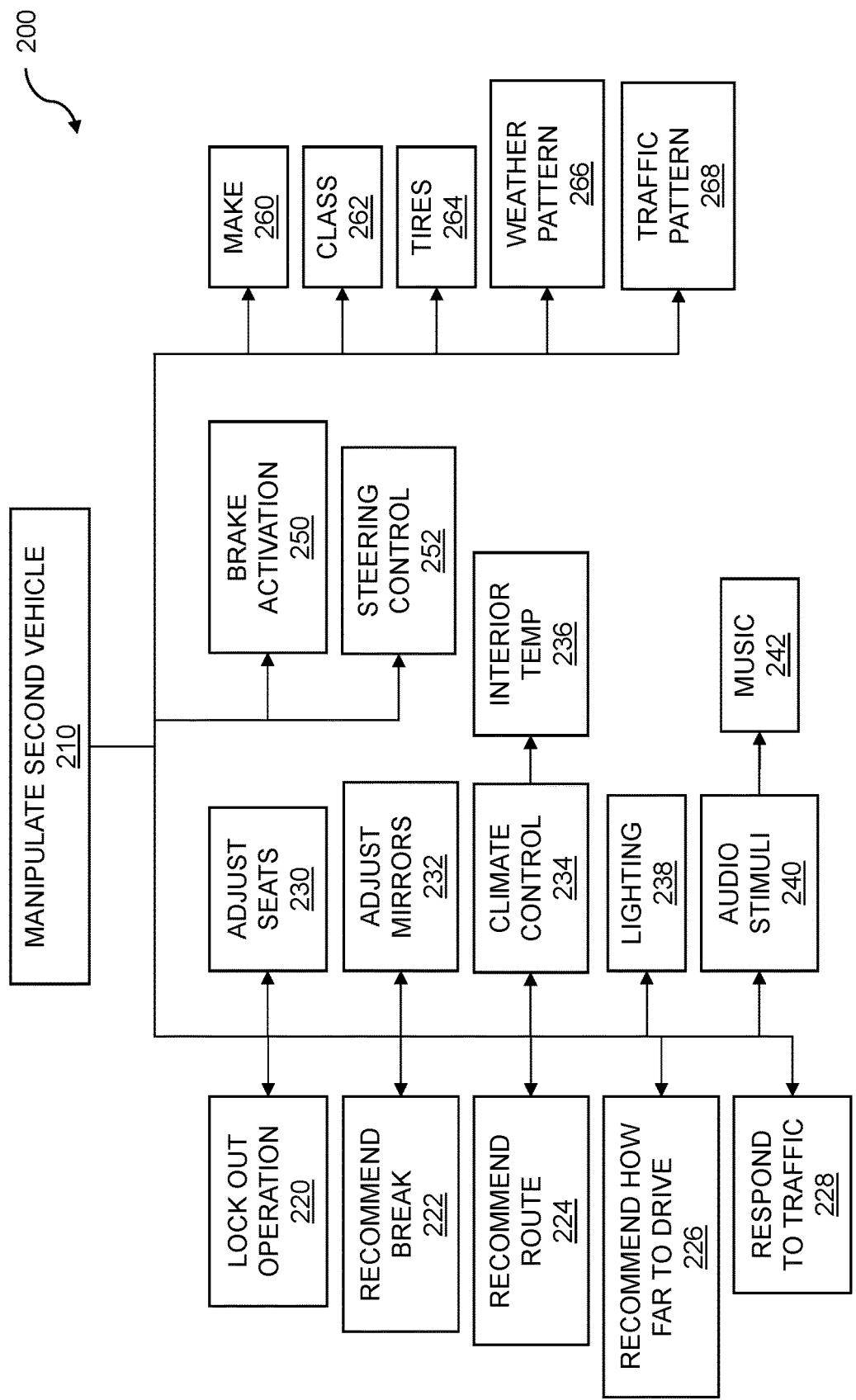
FIG. 2 is a flow diagram for aspects of vehicle manipulation.

FIG. 2 is a flow diagram for aspects of vehicle manipulation. The vehicle manipulation uses occupant image analysis. A camera within a vehicle is used for collecting cognitive state data, including facial data, on an occupant of a vehicle. A cognitive state profile is learned for the occupant based on the cognitive state data. Further cognitive state data on the occupant is captured while the occupant is in a second vehicle. The further cognitive state data is compared with the cognitive state profile that was learned for the occupant. The second vehicle is manipulated based on the comparing. The flow 200 includes manipulating the second vehicle 210 based on the comparing of the further cognitive state data. The manipulating, as discussed below, can control various actions of a vehicle, where a vehicle can be a standard vehicle, a semi-autonomous vehicle, an autonomous vehicle, and so on. In embodiments, the manipulating can include manipulating a first vehicle.

The flow 200 includes a locking out operation 220. The locking out operation can include selectively enabling use of a vehicle, where the selective enabling can include an identity of an occupant in the vehicle. A locking out operation can include enabling and disabling features of the vehicle, preventing the vehicle from being used, and so on. The flow 200 includes recommending a break 222 for the occupant. The recommending a break can be based on elapsed travel time, vehicle operation time, cognitive state such as boredom of the occupant of the vehicle, etc. The recommending a break can include a recommendation for a short break, a stop for a meal, and so on. The flow 200 includes recommending a different route 224. The different route can be recommended due to traffic conditions, weather conditions, an accident, a road closure, the cognitive state of the occupant of the vehicle, and so on. The flow 200 includes recommending how far to drive 226. The recommending how far to drive can include elapsed drive time, difficulty of a travel route, analyzed boredom and inattentiveness of the occupant, anxiety of the occupant, etc. The flow 200 can include responding to traffic 228. Manipulation of the vehicle can include directing the vehicle to a lower traffic route, delaying departure times such as scheduling travel time outside of rush hour times, rerouting the vehicle due to an accident, and so on.

The flow 200 includes manipulating the vehicle for the convenience, needs, preferences, and so on, of the occupant of the vehicle. The flow 200 includes adjusting seats 230 of the vehicle. The adjusting seats can depend on the type of vehicle, the occupant of the vehicle, the preferences of the occupant of the vehicle, and so on. The adjusting the seats can include moving the seat up or down, forward or backward, adjusting seat tilt, adjusting seat temperature, etc. The flow 200 includes adjusting mirrors 232. The mirrors of the vehicle can be adjusted based on the occupant of the vehicle, daytime or nighttime, heavy traffic or light traffic, etc. The flow 200 includes climate control 234. The climate within the vehicle can be controlled based on the occupant of the vehicle, daytime or nighttime, season (e.g. heat or air conditioning), and so on. The climate control can include adjusting interior temperature 236 for a second vehicle. The interior temperature can be adjusted based on the preferences of the occupant of the vehicle, the type of vehicle, etc. The interior temperature manipulation can include manipulating zones within the vehicle. The flow 200 includes lighting 238. The manipulation of the lighting within the vehicle can include light level, color temperature, and so on. The flow 200 includes audio stimuli 240. The audio stimuli can include alerts, warnings, signals, tones, and so on. The audio stimuli can be manipulated based on the cognitive state profile of the occupant of the vehicle. The flow 200 includes manipulating music 242 within the vehicle. The manipulating music can be based on default settings, preferences of the occupant of the vehicle, the cognitive state, mood, and emotion of the occupant, etc.

The flow 200 includes brake activation 250 for the vehicle. Brake activation can include speed control, slowing down, stopping, emergency stopping, and the like. In embodiments, vehicle manipulation can include throttle activation. Throttle activation can include speed control, compensating for hills, accelerating, decelerating, etc. The flow 200 includes steering control 252. Steering control can be used for vehicle manipulation for following a route, changing lanes, making turns, taking evasive action, and so on. In embodiments, the brake activation, throttle activation, or steering control can be manipulated for an autonomous vehicle or a semi-autonomous vehicle. The brake activation, throttle activation, or steering control, can be used for collision avoidance, emergency evasive maneuvers, emergency braking, and the like.

Vehicle manipulation can be performed for a single vehicle, for two vehicles, for multiple vehicles, etc., where the vehicle manipulation can be based on a cognitive state profile of an occupant of the vehicle. In embodiments, the cognitive state profile can be used across a fleet of vehicles. The fleet of vehicles can include automobiles, trucks, sport utility vehicles (SUV), buses, specialty vehicles, and so on. In embodiments, the vehicle (or the first vehicle) and a second vehicle can be the same vehicle. The same vehicle can be operated by multiple operators. In other embodiments, the vehicle and the second vehicle are different vehicles. The vehicle and the second vehicle can be the same type of vehicle, the same particular vehicle, etc. The vehicle and the second vehicle can be part of a fleet of vehicles. The flow 200 includes a vehicle make 260. In embodiments, the vehicles across the fleet of vehicles may have been produced by the same manufacturer, where the manipulation of the vehicles may be handled through a common electrical interface, a common application programming interface (API), and so on. The flow 200 includes a class 262 of vehicle. The class of vehicle can include a compact vehicle, a midsized vehicle, a full-sized vehicle, and so on. The class of vehicle can include another class such as a van, a truck, a bus, a motorcycle, etc. The flow 200 includes the type of tires 264 for vehicle manipulation. The type of tire, such as an all-weather tire, a summer tire, a winter tire, an off-road tire, etc., can be included in determining vehicle speed, braking rate, acceleration rate, choice of route, and so on. The flow 200 includes consideration of a weather pattern 266. The weather pattern can be used to determine vehicle departure time, choice of route to avoid severe weather, choice of route based on elevation or latitude, etc. The flow 200 includes a traffic pattern 268. As for weather and other factors, traffic patterns can be considered for vehicle manipulation. Traffic patterns can be considered for determining departure time, selecting a route of travel, and so on. The manipulation of the second vehicle can be based on the cognitive state profile, as discussed above, and on one or more of the other aspects of vehicle manipulation discussed herein. In embodiments, the manipulating can be based on a make for the second vehicle, a vehicle class for the second vehicle, tires for the second vehicle, a weather pattern, and a traffic pattern. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
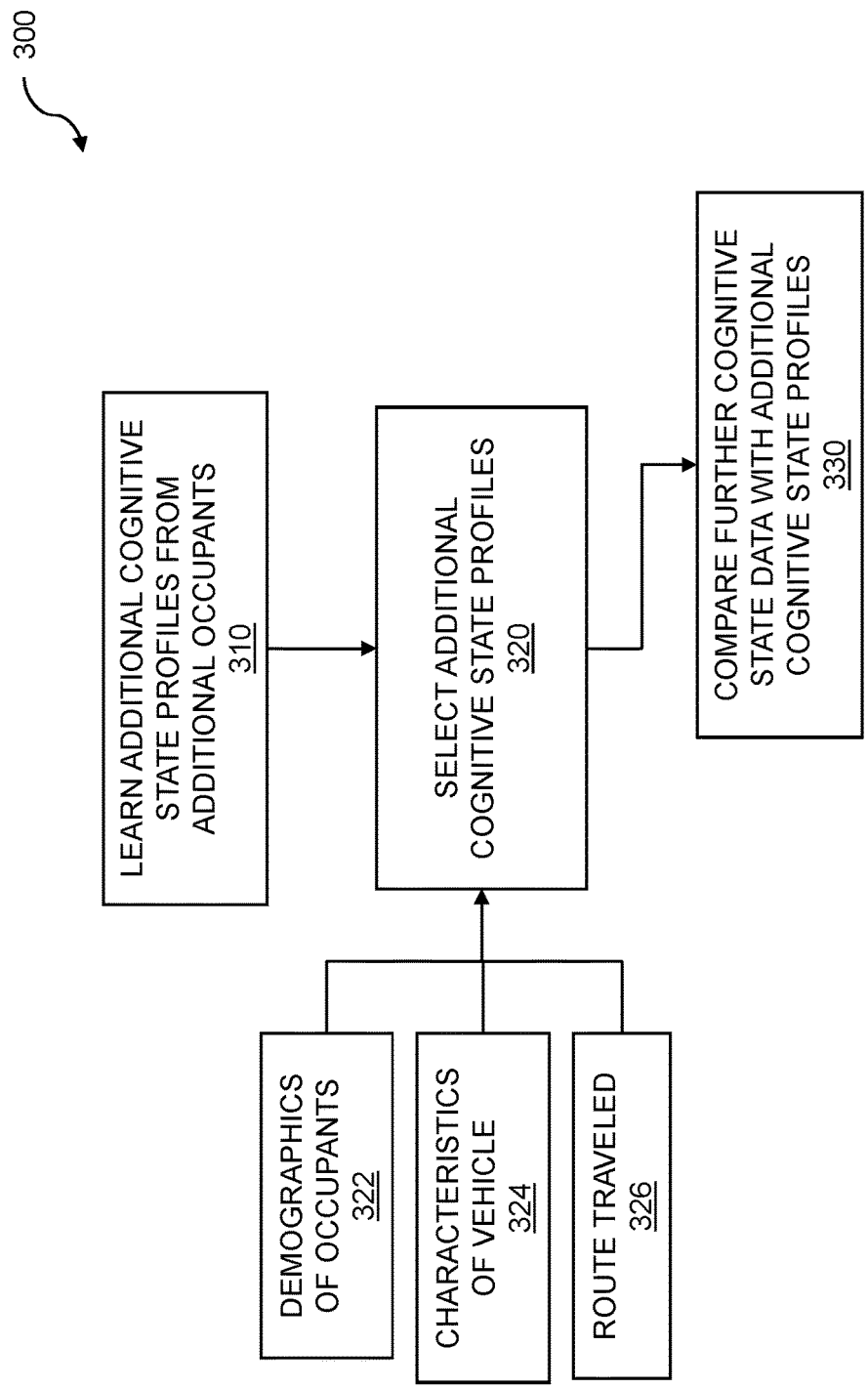
FIG. 3 is a flowchart for selecting cognitive state profiles.

FIG. 3 is a flowchart for selecting cognitive state profiles. Cognitive state profiles can be learned from cognitive state data, can be selected from a plurality of cognitive state profiles, etc. Cognitive state data including facial data is collected on an occupant of a vehicle, and a cognitive state profile is learned. Further cognitive state data is captured and compared with the cognitive state profile. A vehicle is manipulated based on the comparing of the further cognitive state data. A vehicle, such as the second vehicle, can be manipulated using occupant image analysis. Further cognitive state can be collected from other occupants, where the other occupants can be in the same vehicle as the first occupant, in one or more vehicles different from the one in which the first occupant is present, etc. The flow 300 includes learning additional cognitive state profiles from additional occupants 310 of additional vehicles. The learning additional cognitive state profiles can be based on collecting cognitive state data such as facial data, voice data, audio data, and the like. The cognitive state data can include physiological data such as heart rate or heart rate variability, acceleration data, etc.

The flow 300 includes selecting additional cognitive state profiles 320. The cognitive state profiles can be learned, retrieved from a library of cognitive state profiles, downloaded from a computer network, uploaded by a user, and so on. In embodiments, the additional cognitive state profiles can be selected based on demographics 322 of the occupant. Demographics of the occupant can include age, race, gender, ethnicity, geographic location, income level, and the like. The demographics can be derived, predicted, self-identified by the occupant, etc. The demographics of the occupant can be based on an occupant profile or identification (ID). In embodiments, the additional cognitive state profiles can be selected based on characteristics of the vehicle 324 of the occupant. The characteristics of the vehicle can include type of vehicle such as automobile, airplane, train, a private vehicle, a fleet vehicle, public transportation, hired transportation, etc. In further embodiments, the additional cognitive state profiles can be selected based on a route 326 being travelled. The route being travelled can include a commuting route, a highway, a secondary road, a sightseeing route, and so on. The route being travelled can present travel problems such as weather, traffic, accidents, and so on. The detection of the cognitive state profile can be based on cognitive state data, where the cognitive state data can be used in detection of one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In some cases, the impacts on cognitive state can be varied including an interaction that the occupant is having with another occupant or that the occupant is having on a cell phone or other mobile device. The flow 300 further includes comparing the further cognitive state data with additional cognitive state profiles 330 learned from additional occupants of additional vehicles. The comparing the further cognitive state data can be used for manipulating the second vehicle or another vehicle, for choosing a travel route, for climate control within a vehicle, and so on.

Figure 4:
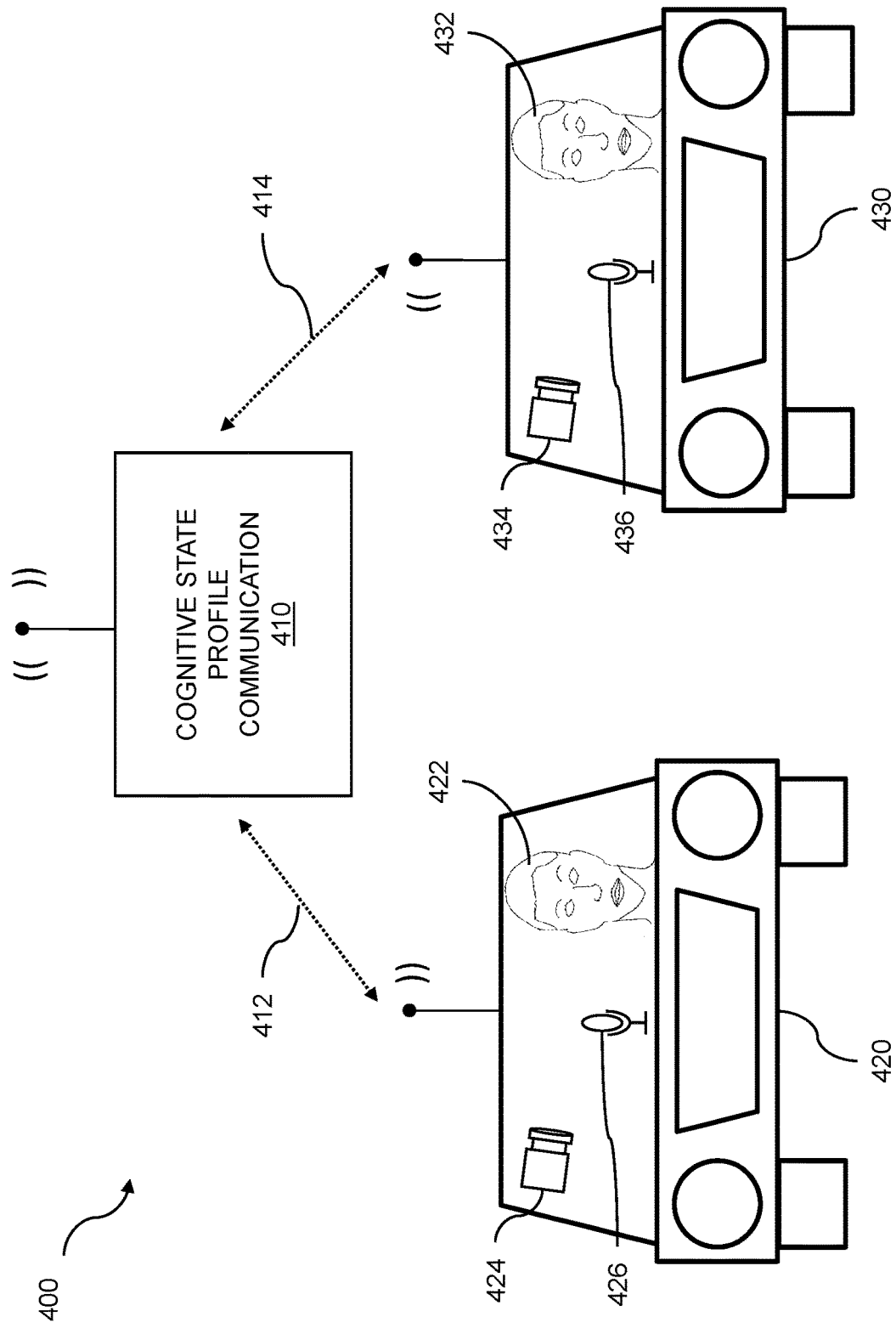
FIG. 4 is a system diagram for vehicle manipulation.

FIG. 4 is a system diagram for vehicle manipulation. Vehicle manipulation can use occupant image analysis. A camera within a vehicle is used to collect cognitive state data including facial data, on an occupant of a vehicle. A cognitive state profile is learned for the occupant. Further cognitive state data on the occupant is captured while the occupant is in a second vehicle. The further cognitive state data is compared with the cognitive state profile, and the second vehicle is manipulated based on the comparing of the further cognitive state data. A system 400 for vehicle manipulation is shown. The system can include cognitive state profile communication 410. The communicating of the cognitive state profile communication can include sending cognitive state profile information to a first vehicle 420, to a second vehicle 430, and so on. The cognitive state profile communication can include manipulating the first vehicle 420, the second vehicle 430, etc. The manipulating can include a locking out operation; recommending a break for the occupant; recommending a different route; recommending how far to drive; responding to traffic; adjusting seats, mirrors, climate control, lighting, music, audio stimuli, interior temperature for the second vehicle; brake activation; steering control; and other vehicle control and manipulation techniques.

The cognitive state profile can be sent to a first vehicle 420 using a wireless link 412 or other data transfer technique. The cognitive state profile that can be sent can be based on cognitive state data including facial data from an occupant 422 of the first vehicle 420. The cognitive state data including facial data can be collected using a camera 424 or other image capture technique. The system 400 can include collecting voice data and augmenting the cognitive state data with the voice data. The voice data can be collected from the occupant 422 using a microphone 426 or other audio capture technique. The voice data can include audio data, where the audio data can include traffic sounds, road noise, music, news, eBooks, etc., that can be played by the occupant, and so on. The system 400 can include evaluating the voice data for timbre, prosody, vocal register, vocal resonance, pitch, loudness, speech rate, or language content. The evaluating the voice data can also be used in evaluating the cognitive state or states of the occupant 422 of the first vehicle 420. In embodiments, the augmenting can be based on lexical analysis of the voice data that looks at sentiment. As for the first vehicle, the cognitive state profile can be sent to a second vehicle 430 using a wireless link 414 or other data transfer technique. The cognitive state profile can be based on cognitive state data including facial data from an occupant 432 of the second vehicle 430, can be based on the cognitive state data including facial data from the occupant 422 of the first vehicle 420, and so on. The cognitive state data including facial data can be collected using a camera 434 or other image capture technique. The system 400 can include collecting voice data from the occupant 432 using a microphone 436 or other audio capture technique.

Figure 5:
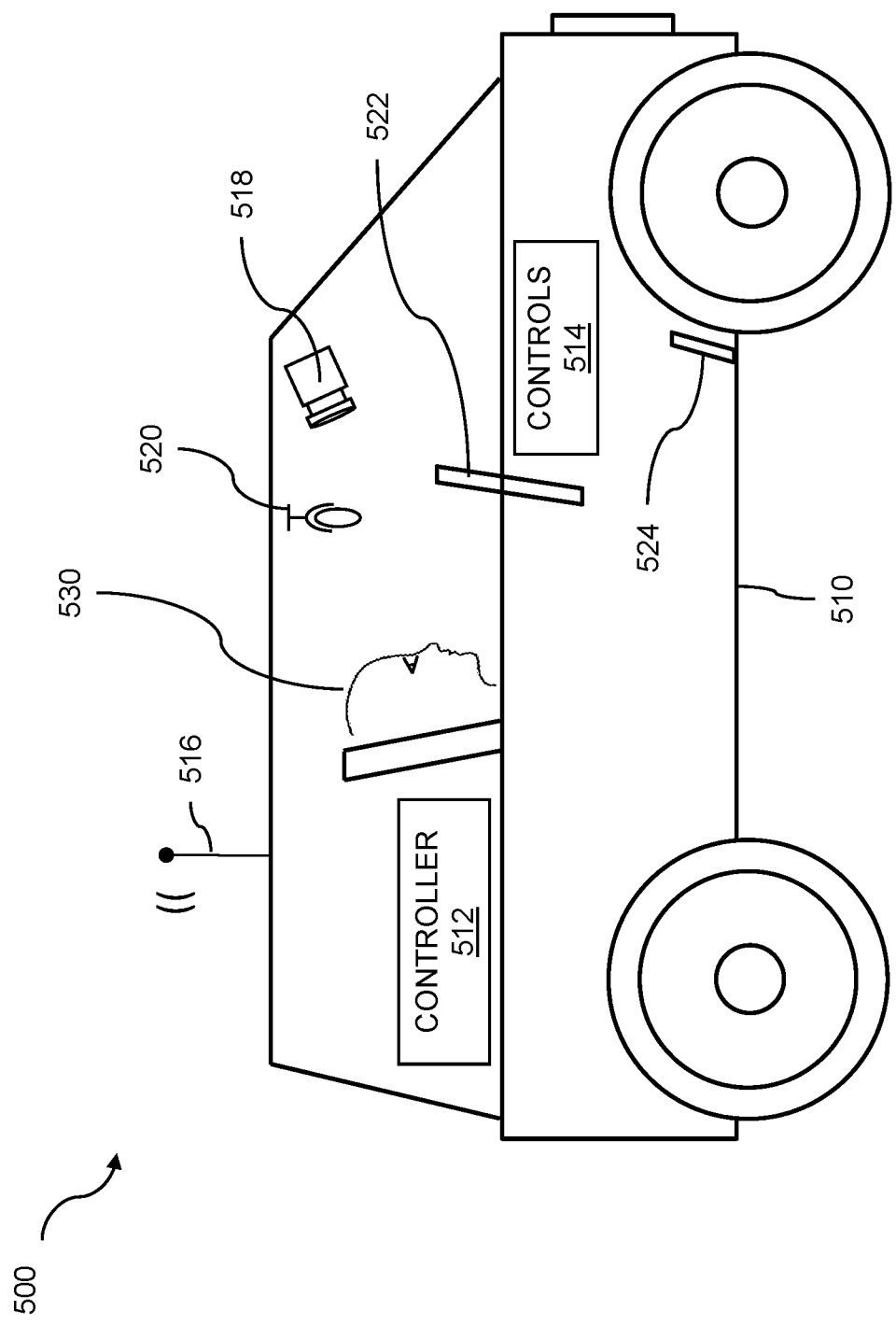
FIG. 5 is a system diagram for an interior of a vehicle.

FIG. 5 is a system diagram for an interior of a vehicle 500. Vehicle manipulation can be based on using occupant image analysis. A camera within a vehicle is used for collecting cognitive state data, including facial data, on an occupant of a vehicle. A cognitive state profile is learned for the occupant based on the cognitive state data. Further cognitive state data on the occupant is captured while the occupant is in a second vehicle. The further cognitive state data is compared with the cognitive state profile. The second vehicle is manipulated based on the comparing of the further cognitive state data. An occupant 530 of a vehicle 510 can be observed using a camera 518, a microphone 520, and other image and audio capture techniques. The image data can include video data. The video data and the audio data can include cognitive state data where the cognitive state data can include facial data. The occupant can be a driver of the vehicle 510, a passenger within the vehicle, and so on.

The interior of a vehicle 510 can be a standard vehicle, an autonomous vehicle, a semi-autonomous vehicle, and so on. The vehicle can be an automobile, a van, a sport utility vehicle (SUV), a truck, a bus, a special purpose vehicle, etc. The interior of the vehicle 510 can include standard controls such as a steering wheel 522, a throttle control (not shown), a brake 524, and so on. The interior of the vehicle can include other controls 514 such as controls for seats, mirrors, climate controls, etc. The controls 514 of the vehicle 510 can be controlled by a controller 512. The controller 512 can control the vehicle 510 in various manners such as autonomously, semi-autonomously, assertively to a vehicle occupant 530, etc. In embodiments, the controller provides no vehicle control techniques, assistance, etc. The controller 512 can receive instructions via an antenna 516 or using other wireless techniques. The controller 512 can be pre-programmed to cause the vehicle to follow a specific route.

Figure 6:
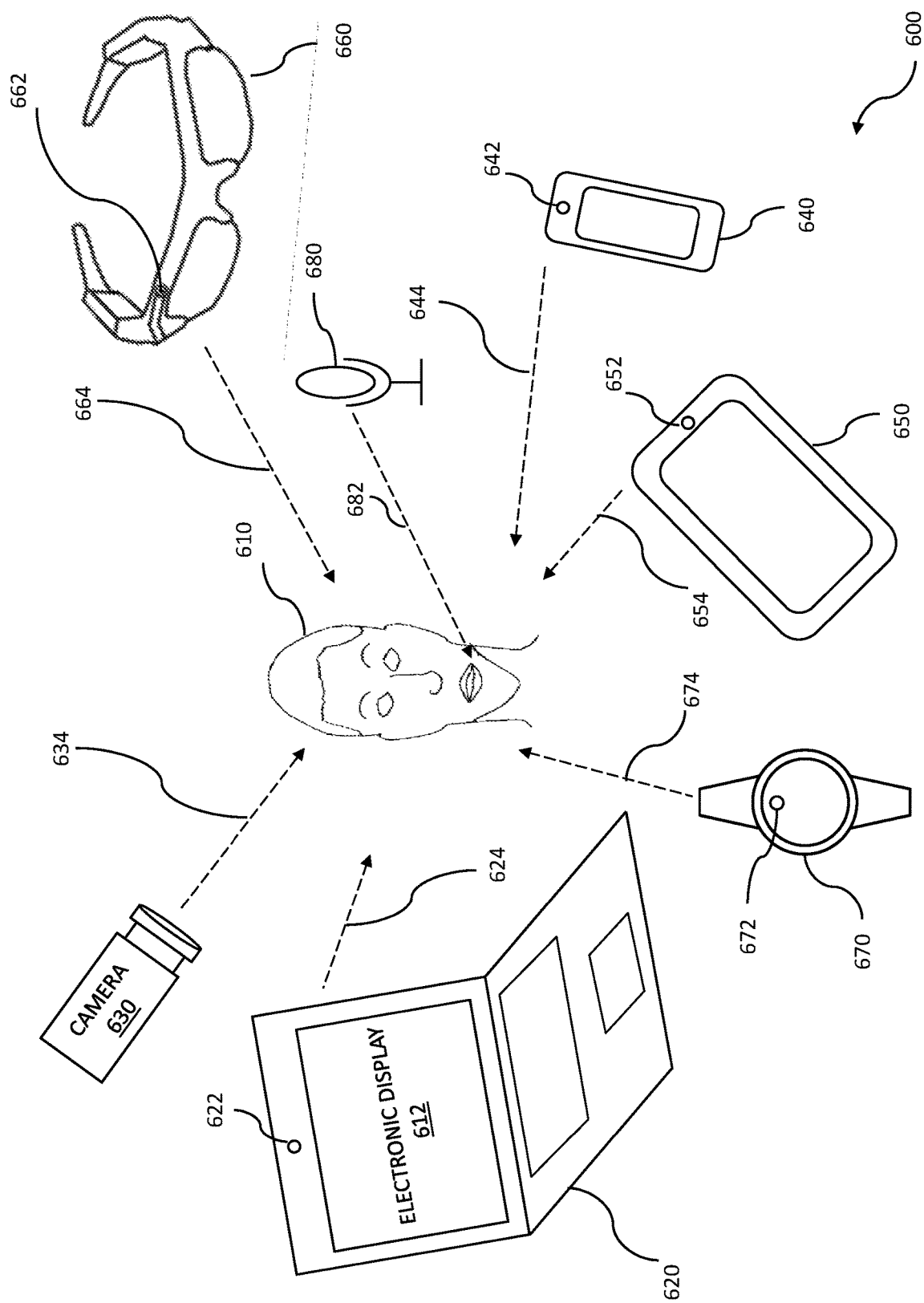
FIG. 6 is a diagram showing image collection including multiple mobile devices.

FIG. 6 shows example image and audio collection including multiple mobile devices. Cognitive state data including image data and audio data can be collected using multiple mobile devices. The collected cognitive state data can be used for vehicle manipulation using occupant image analysis. A cognitive state profile can be learned, and further cognitive state data can be collected from an individual while in a second vehicle. The further cognitive state data can be compared to the cognitive state profile, and the second vehicle can be manipulated based on the comparing. While one person is shown, in practice the video data on any number of people can be collected. In the diagram 600, the multiple mobile devices can be used separately or in combination to collect video data, audio data, or both video data and audio data on a user 610. While one person is shown, the video data and audio data can be collected on multiple people. A user 610 can be observed as she or he is performing a task, experiencing an event, viewing a media presentation, and so on. The user 610 can be shown one or more media presentations, political presentations, social media, or another form of displayed media. The one or more media presentations can be shown to a plurality of people. The media presentations can be displayed on an electronic display 612 or another display. The data collected on the user 610 or on a plurality of users can be in the form of one or more videos, video frames, still images, one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations and viewing either a single media presentation or a plurality of presentations. The data collected on the user 610 can be analyzed and viewed for a variety of purposes including expression analysis, cognitive state analysis, mental state analysis, emotional state analysis, and so on. The electronic display 612 can be on a laptop computer 620 as shown, a tablet computer 650, a cell phone 640, a television, a mobile monitor, or any other type of electronic device. In one embodiment, video data including expression data is collected on a mobile device such as a cell phone 640, a tablet computer 650, a laptop computer 620, or a watch 670. Similarly, the audio data including speech data and non-speech vocalizations can be collected on one or more of the mobile devices. Thus, the multiple sources can include at least one mobile device, such as a smartphone or cell phone 640 or a tablet 650, or a wearable device such as a watch 670 or glasses 660. A mobile device can include a forward-facing camera and/or a back-side camera that can be used to collect expression data. A mobile device can include a microphone, audio transducer, or other audio capture apparatus that can be used to capture the speech and non-speech vocalizations. Sources of expression data can include a webcam 622, a phone camera 642, a tablet camera 652, a wearable camera 662, and a mobile camera 630. A wearable camera can comprise various camera devices, such as a watch camera 672. Sources of audio data 682 can include a microphone 680.

As the user 610 is monitored, the user 610 might move due to the nature of the task, boredom, discomfort, distractions, or for another reason. As the user moves, the camera with a view of the user's face can be changed. Thus, as an example, if the user 610 is looking in a first direction, the line of sight 624 from the webcam 622 is able to observe the user's face, but if the user is looking in a second direction, the line of sight 634 from the mobile camera 630 is able to observe the user's face. Furthermore, in other embodiments, if the user is looking in a third direction, the line of sight 644 from the phone camera 642 is able to observe the user's face, and if the user is looking in a fourth direction, the line of sight 654 from the tablet camera 652 is able to observe the user's face. If the user is looking in a fifth direction, the line of sight 664 from the wearable camera 662, which can be a device such as the glasses 660 shown and can be worn by another user or an observer, is able to observe the user's face. If the user is looking in a sixth direction, the line of sight 674 from the wearable watch-type device 670, with a camera 672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 610 can also use a wearable device including a camera for gathering contextual information and/or collecting expression data on other users. Because the user 610 can move her or his head, the facial data can be collected intermittently when she or he is looking in a direction of a camera. In some cases, multiple people can be included in the view from one or more cameras, and some embodiments include filtering out faces of one or more other people to determine whether the user 610 is looking toward a camera. All or some of the expression data can be continuously or sporadically available from the various devices and other devices.

The captured video data can include facial expressions, and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 7:
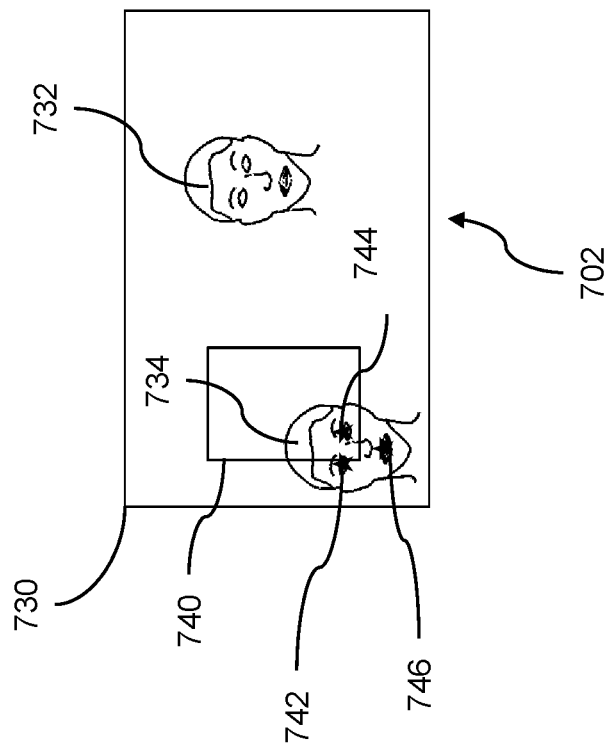
FIG. 7 illustrates feature extraction for multiple faces.
Figure 7:
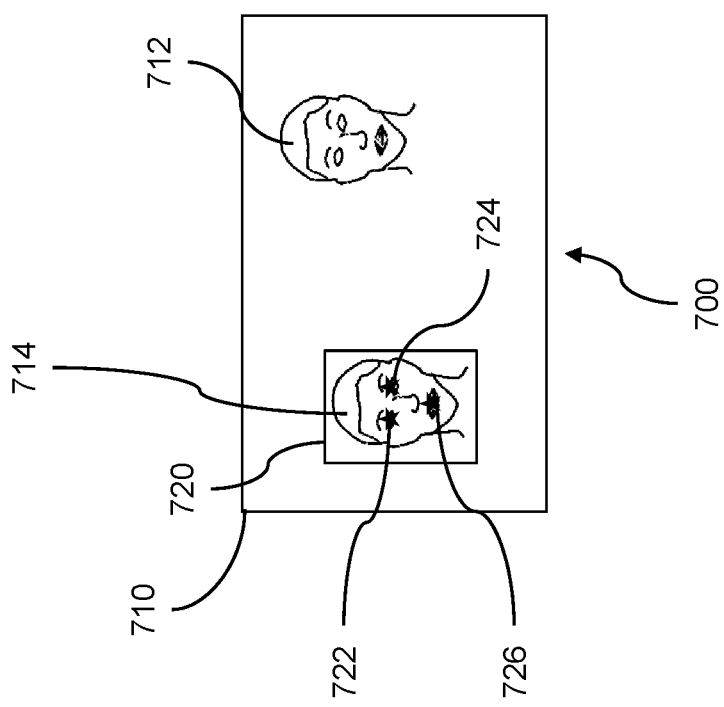

FIG. 7 illustrates feature extraction for multiple faces. Image analysis, including facial analysis, can be based on feature extraction from multiple faces. Vehicle manipulation uses occupant image analysis. A vehicle camera is used for collecting cognitive state data including facial data on an occupant of a vehicle. A cognitive state profile is learned for the occupant. Further cognitive state data is captured while the occupant is in a second vehicle, and the further cognitive state data is compared with the learned cognitive state profile. The second vehicle is manipulated based on the comparing of the further cognitive state data. The feature extraction for multiple faces can be performed for faces that can be detected in multiple images. In embodiments, the features of multiple faces are extracted for evaluating cognitive states. Features of a face or a plurality of faces can be extracted from collected video data. The feature extraction can be performed by analysis, using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in a single frame or in multiple frames of one or more videos.

Returning to FIG. 7, the detection of the first face, the second face, and multiple faces can include identifying facial landmarks, generating a bounding box, and predicting a bounding box and landmarks for a next frame, where the next frame can be one of a plurality of frames of a video containing faces. A first video frame 700 includes a frame boundary 710, a first face 712, and a second face 714. The video frame 700 also includes a bounding box 720. Facial landmarks can be generated for the first face 712. Face detection can be performed to initialize a second set of locations for a second set of facial landmarks for a second face within the video. Facial landmarks in the video frame 700 can include the facial landmarks 722, 724, and 726. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 720. Bounding boxes can also be estimated for one or more other faces within the boundary 710. The bounding box can be refined, as can one or more facial landmarks. The refining of the second set of locations for the second set of facial landmarks can be based on localized information around the second set of facial landmarks. The bounding box 720 and the facial landmarks 722, 724, and 726 can be used to estimate future locations for the second set of locations for the second set of facial landmarks in a future video frame from the first video frame.

A second video frame 702 is also shown. The second video frame 702 includes a frame boundary 730, a first face 732, and a second face 734. The second video frame 702 also includes a bounding box 740 and the facial landmarks, or points, 742, 744, and 746. In other embodiments, multiple facial landmarks are generated and used for facial tracking of the two or more faces of a video frame, such as the shown second video frame 702. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 740 can be estimated, where the estimating can be based on the location of the generated bounding box 720 shown in the first video frame 700. The three facial points shown, facial points, or landmarks, 742, 744, and 746, might lie within the bounding box 740 or might not lie partially or completely within the bounding box 740. For instance, the second face 734 might have moved between the first video frame 700 and the second video frame 702. Based on the accuracy of the estimating of the bounding box 740, a new estimation can be determined for a third, future frame from the video, and so on. The evaluation can be performed, all or in part, using semiconductor-based logic.

Figure 8:
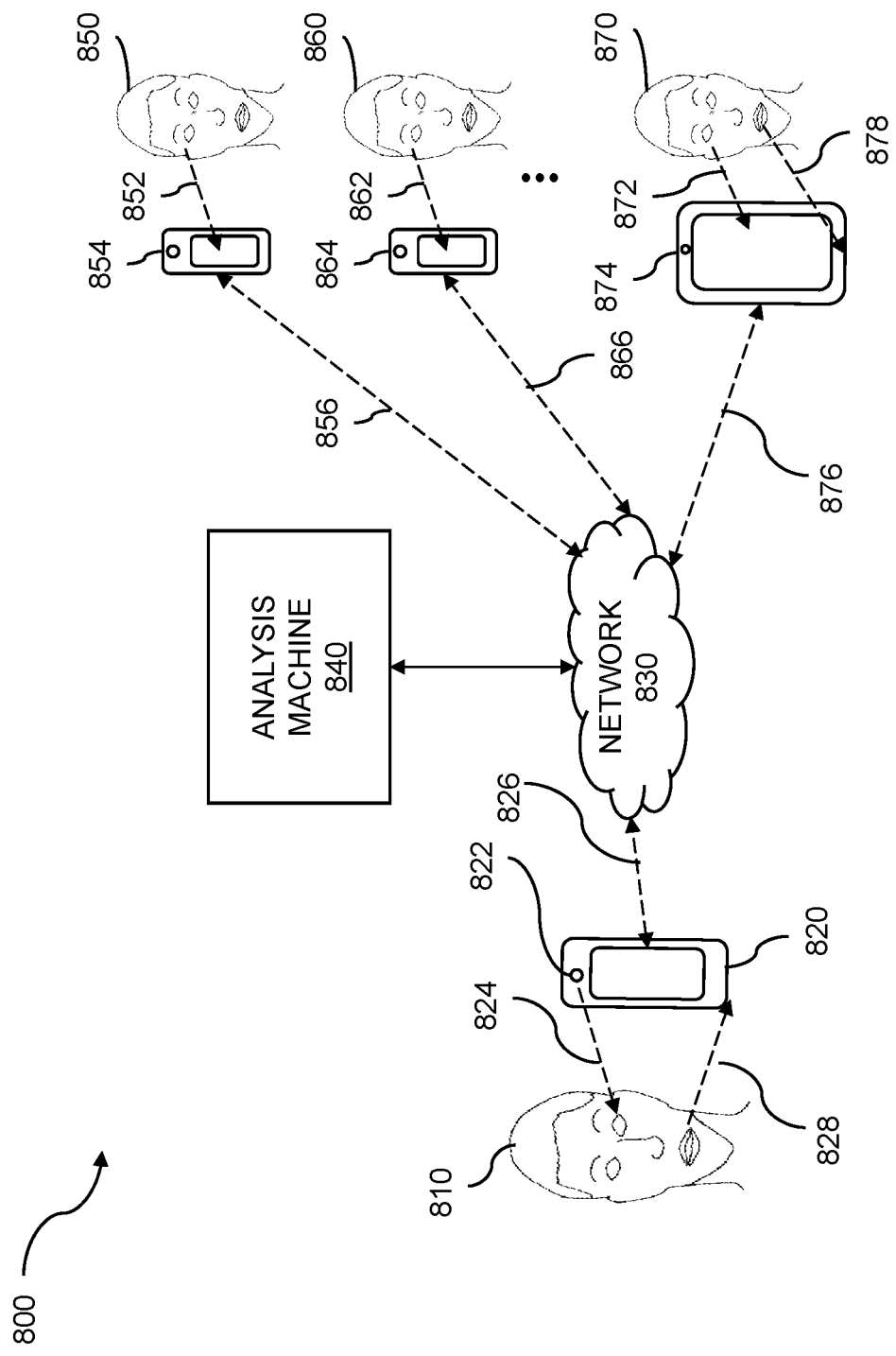
FIG. 8 shows an example of live streaming of social video and audio.

FIG. 8 shows an example of live streaming of social video and audio. The streaming of social video and social audio can be applied to vehicle manipulation using occupant image analysis. The live streaming can include cognitive state data, facial data, speech data, audio data, etc. The cognitive state data can be obtained on an occupant of a vehicle and used for learning a cognitive state profile. Further cognitive state data can be collected on the individual while in a second vehicle, and the further data can be compared with the cognitive state profile. The second vehicle can be manipulated based on the comparing the further cognitive state data.

The live streaming and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and acknowledged by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 800 shows a user 810 broadcasting a video live stream and an audio live stream to one or more people as shown by a first person 850, a second person 860, and a third person 870. A portable, network-enabled, electronic device 820 can be coupled to a front-side camera 822. The portable electronic device 820 can be a smartphone, a PDA, a tablet, a laptop computer, and so on. The front-side camera 822 coupled to the device 820 can have a line-of-sight view 824 to the user 810 and can capture video of the user 810. The portable electronic device 820 can be coupled to a microphone (not shown). The microphone can capture voice data 828 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 840 using a network link 826 to the Internet 830. The network link can be a wireless link, a wired link, and so on. The recommendation engine 840 can recommend to the user 810 an app and/or platform that can be supported by the server and can be used to provide a video live stream, an audio live stream, or both a video live stream and an audio live stream to one or more followers of the user 810.

In the example 800, the user 810 has three followers: a first person 850, a second person 860, and a third person 870. Each follower has a line-of-sight view to a video screen on a portable, networked electronic device. In other embodiments, one or more followers follow the user 810 using any other networked electronic device, including a computer. In the example 800, a first person 850 has a line-of-sight view 852 to the video screen of a device 854; a second person 860 has a line-of-sight view 862 to the video screen of a device 864, and a third person 870 has a line-of-sight view 872 to the video screen of a device 874. The device 874 can also capture audio data 878 from the third person 870. The portable electronic devices 854, 864, and 874 can each be a smartphone, a PDA, a tablet, and so on. Each portable device can receive the video stream and the audio stream being broadcast by the user 810 through the Internet 830 using the app and/or platform that can be recommended by the recommendation engine 840. The device 854 can receive a video stream and the audio stream using the network link 856, the device 864 can receive a video stream and the audio stream using the network link 866, the device 874 can receive a video stream and the audio stream using the network link 876, and so on. The network link can be a wireless link, a wired link, a hybrid link, and so on. Depending on the app and/or platform that can be recommended by the recommendation engine 840, one or more followers, such as the followers shown 850, 860, and 870, can reply to, comment on, or otherwise provide feedback to the user 810 using their respective devices 854, 864, and 874.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 9:
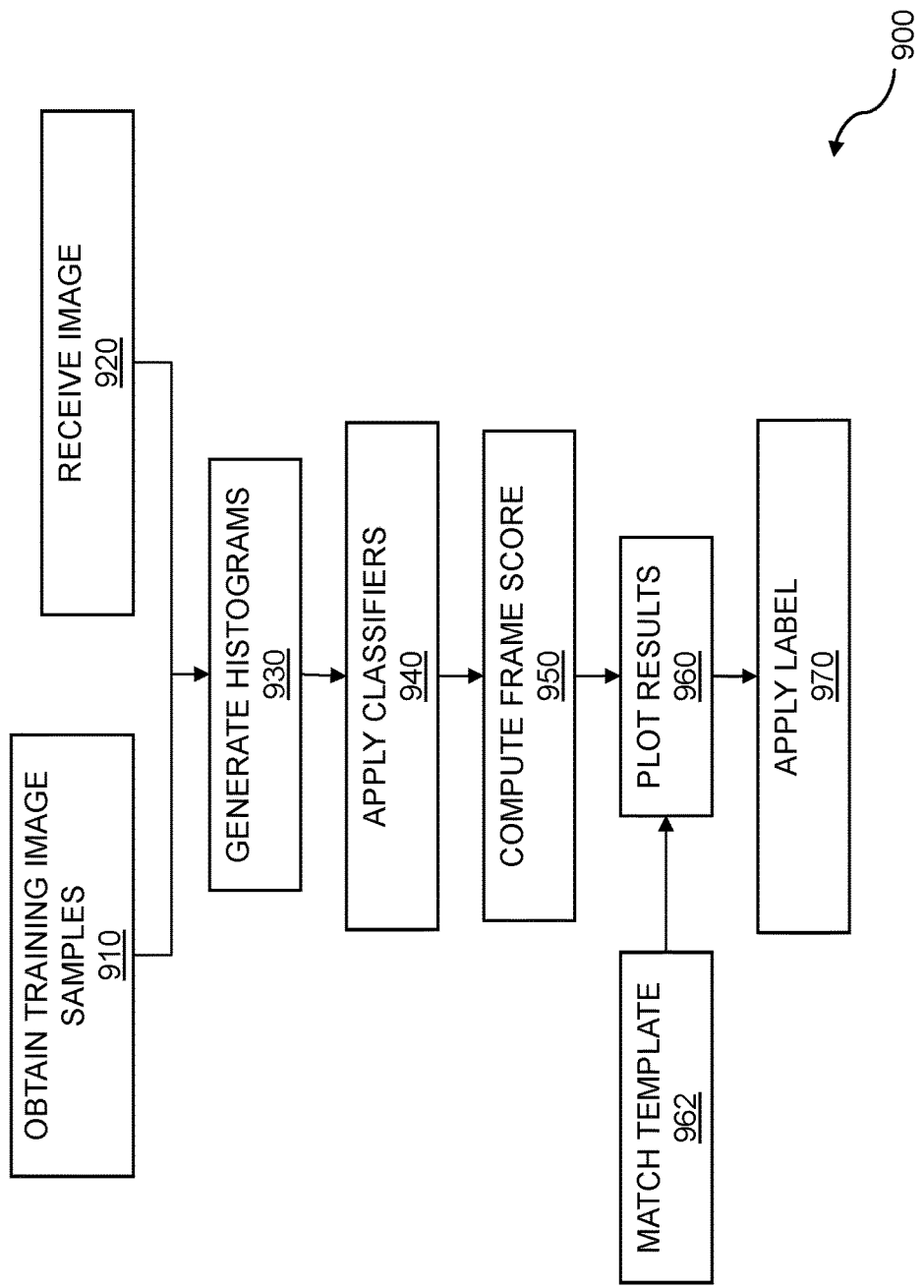
FIG. 9 is a flow diagram for detecting facial expressions.

FIG. 9 is a flow diagram for detecting facial expressions. Cognitive states can be determined by detecting and analyzing facial expressions in images. Vehicle manipulation can be based on using occupant image analysis. Cognitive state data including facial data is collected an occupant of a vehicle, and a cognitive state profile is learned for the occupant. Further cognitive state data on the occupant is captured while the occupant is in a second vehicle. The further cognitive state data is captured in a second vehicle and compared with the cognitive state profile. The second vehicle is manipulated based on the comparing of the further cognitive state data. The flow 900, or portions thereof, can be implemented in semiconductor logic, can be accomplished using a mobile device, can be accomplished using a server device, and so on. The flow 900 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 900 begins by obtaining training image samples 910. The image samples can include a plurality of images of one or more people. Human coders who are trained to correctly identify AU codes based on the FACS can code the images. The training, or "known good", images can be used as a basis for training a machine learning technique. Once trained, the machine learning technique can be used to identify AUs in other images that can be collected using a camera, a sensor, and so on. The flow 900 continues with receiving an image 920. The image can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 900 continues with generating histograms 930 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 900 continues with applying classifiers 940 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 900 continues with computing a frame score 950. The score computed for an image, where the image can be a frame from a video, can be used to determine the presence of a facial expression in the image or video frame. The score can be based on one or more versions of the image or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier can be used to identify symmetrical facial expressions (e.g. smile), asymmetrical facial expressions (e.g. outer brow raiser), and so on.

The flow 900 continues with plotting results 960. The plotted results can include one or more scores for one or more frames computed over a given time t. For example, the plotted results can include classifier probability results from analysis of HoGs for a sequence of images and video frames. The plotted results can be matched with a template 962. The template can be temporal and can be represented by a centered box function or another function. A best fit with one or more templates can be found by computing a minimum error. Other best-fit techniques can include polynomial curve fitting, geometric curve fitting, and so on. The flow 900 continues with applying a label 970. The label can be used to indicate that a particular facial expression has been detected in the one or more images or video frames which constitute the image that was received 920. The label can be used to indicate that any of a range of facial expressions has been detected, including a smile, an asymmetric smile, a frown, and so on. Various steps in the flow 900 may be changed in order, repeated, omitted, or the like without departing from the disclosed concepts. Various embodiments of the flow 900 can be included in a computer program product embodied in a non-transitory computer readable medium that includes code executable by one or more processors. Various embodiments of the flow 900, or portions thereof, can be included on a semiconductor chip and implemented in special purpose logic, programmable logic, and so on.

Figure 10:
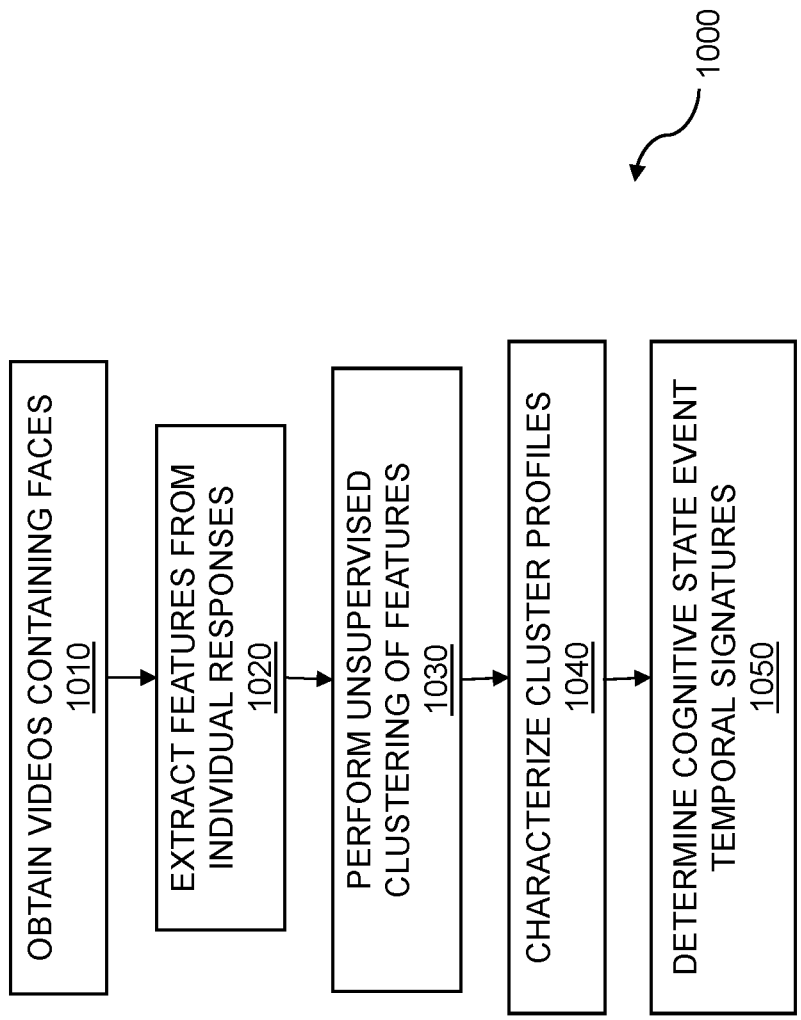
FIG. 10 is a flow diagram for the large-scale clustering of facial events.

FIG. 10 is a flow diagram for the large-scale clustering of facial events. Vehicle manipulation can be based on using occupant image analysis and can use results from large-scale clustering. A camera is used for collecting cognitive state data on an occupant of a vehicle. A cognitive state profile is learned for the occupant. Further cognitive state data is captured while the occupant is in a second vehicle. The further cognitive state data is compared with the cognitive state profile, and the second vehicle is manipulated based on the comparing. Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1000 includes obtaining videos containing faces 1010. The videos can be obtained using one or more cameras, where the cameras can include a webcam coupled to one or more devices employed by the one or more people using the web-based framework. The flow 1000 continues with extracting features from the individual responses 1020. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1000 continues with performing unsupervised clustering of features 1030. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1000 includes characterizing cluster profiles 1040. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1000 can include determining cognitive state event temporal signatures 1050. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
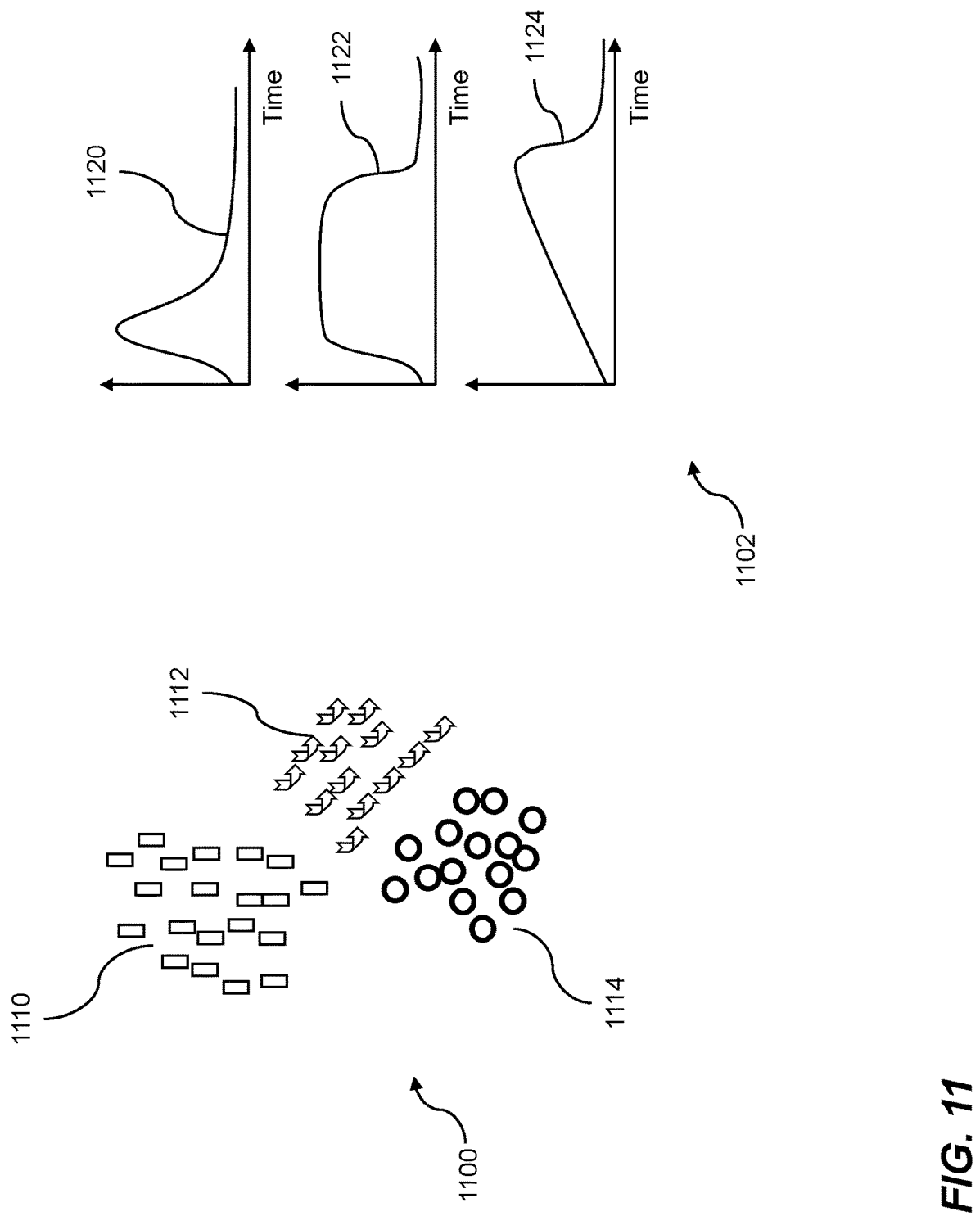
FIG. 11 shows unsupervised clustering of features and characterizations of cluster profiles.

FIG. 11 shows unsupervised clustering of features and characterizations of cluster profiles. Vehicle manipulation can be initiated using occupant image analysis based on clustering. A camera within a vehicle is used for collecting cognitive state data on an occupant of a vehicle. A cognitive state profile is learned for the occupant. Further cognitive state data on the occupant is captured while the occupant is in a second vehicle. The further cognitive state data is compared with the cognitive state profile, and the second vehicle is manipulated based on the comparing. The clustering of features and characterizations of cluster profiles can be performed for data collected from a remote computing device. The clustering of features and characterizations of cluster profiles can be performed for people as they interact with a vehicle. The sub-sectional components can be used with performing the evaluation of content of the face. The sub-sectional components can be used to provide a context. Features including samples of facial data can be clustered using unsupervised clustering. Various clusters can be formed which include similar groupings of facial data observations. The example 1100 shows three clusters, clusters 1110, 1112, and 1114. The clusters can be based on video collected from people who have opted-in to video collection. When the data collected is captured using a web-based framework, the data collection can be performed on a grand scale, including hundreds, thousands, or even more participants who can be situated locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1102 can be generated based on the clusters that can be formed from unsupervised clustering, with time shown on the x-axis and intensity or frequency shown on the y-axis. The cluster profiles can be based on captured facial data, including facial expressions. The cluster profile 1120 can be based on the cluster 1110, the cluster profile 1122 can be based on the cluster 1112, and the cluster profile 1124 can be based on the cluster 1114. The cluster profiles 1120, 1122, and 1124 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 12A:
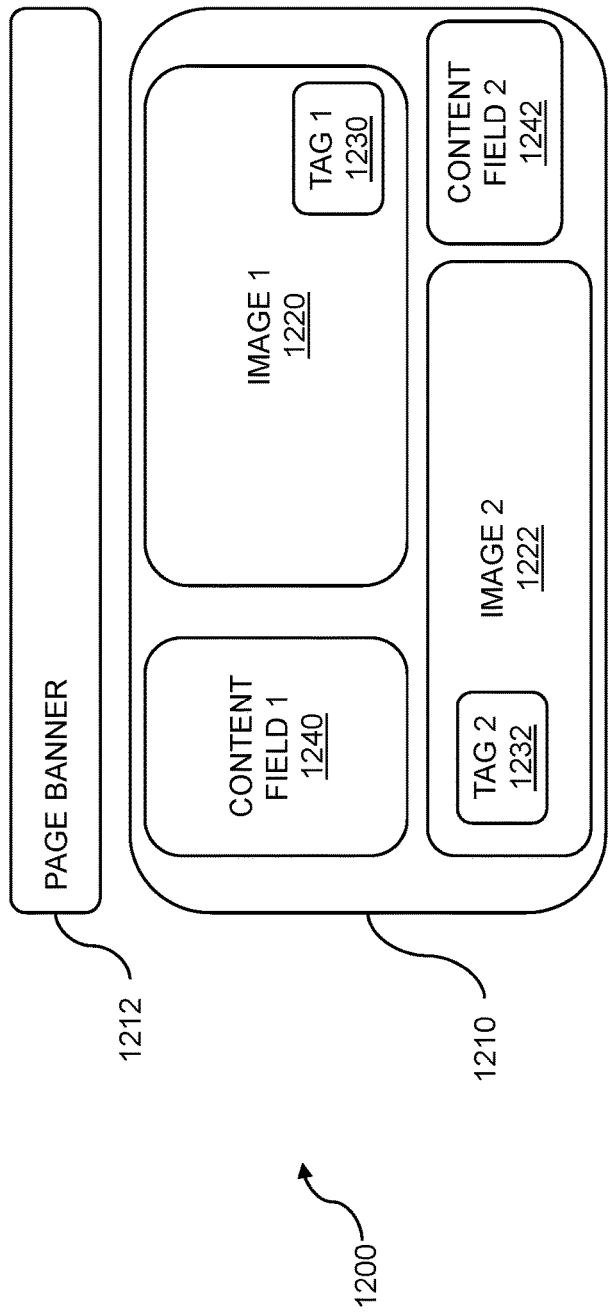
FIG. 12A shows example tags embedded in a webpage.

FIG. 12A shows example tags embedded in a webpage. Vehicle manipulation can be based on using occupant image analysis. In some embodiments, screens within a vehicle can use embedded tags. A camera within a vehicle is used for collecting cognitive state data including facial data, on an occupant of a vehicle. A cognitive state profile is learned for the occupant. Further cognitive state data is captured while the occupant is in a second vehicle. The further cognitive state data is compared with the cognitive state profile, and the second vehicle is manipulated based on the comparing. The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1200 can include a page body 1210, a page banner 1212, and so on. The page body can include one or more objects, where the objects can include text, images, videos, audio, and so on. The example page body 1210 shown includes a first image, image 1 1220; a second image, image 2 1222; a first content field, content field 1 1240; and a second content field, content field 2 1242. In practice, the page body 1210 can contain multiple images and content fields and can include one or more videos, one or more audio presentations, and so on. The page body can include embedded tags, such as tag 1 1230 and tag 2 1232. In the example shown, tag 1 1230 is embedded in image 1 1220, and tag 2 1232 is embedded in image 2 1222. In embodiments, multiple tags are imbedded. Tags can also be embedded in content fields, in videos, in audio presentations, etc. When a user mouses over a tag or clicks on an object associated with a tag, the tag can be invoked. For example, when the user mouses over tag 1 1230, tag 1 1230 can then be invoked. Invoking tag 1 1230 can include enabling a camera coupled to a user's device and capturing one or more images of the user as the user views a media presentation (or digital experience). In a similar manner, when the user mouses over tag 2 1232, tag 2 1232 can be invoked. Invoking tag 2 1232 can also include enabling the camera which can capture images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 12B:
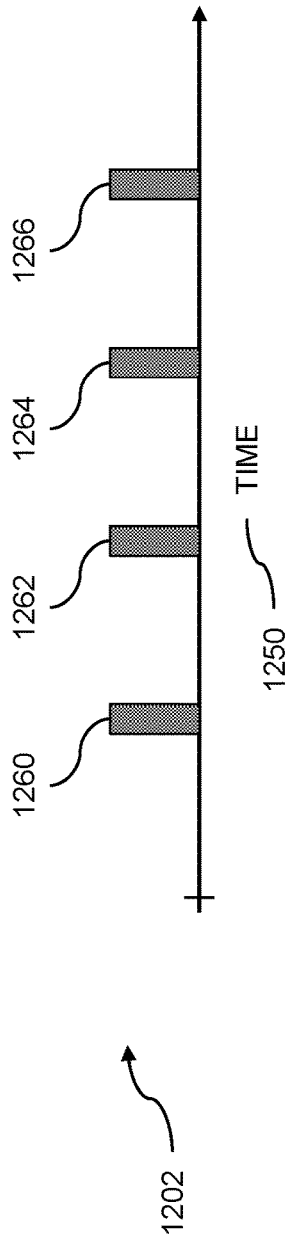
FIG. 12B shows invoking tags to collect images.

FIG. 12B shows invoking tags to collect images. Vehicle manipulation can be based on using occupant image analysis. The occupant image analysis is based on collecting cognitive state data from the occupant and learning a cognitive state profile. Further cognitive state data is collected and compared to the cognitive state profile. A second vehicle is manipulated based on the comparing. The invoking tags to collect images can be used for image analysis for data collected from a remote computing device. The invoking tags to collect images can be used for people as they interact with a vehicle. As previously stated, a media presentation can be a video, a webpage, and so on. A video 1202 can include one or more embedded tags, such as a tag 1260, another tag 1262, a third tag 1264, a fourth tag 1266, and so on. In practice, multiple tags can be included in the media presentation. The one or more tags can be invoked during the media presentation. The collection of the invoked tags can occur over time, as represented by a timeline 1250. When a tag is encountered in the media presentation, the tag can be invoked. When the tag 1260 is encountered, invoking the tag can enable a camera coupled to a user device which can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has indicated an opt-out, then invoking the tag 1260 does not enable the camera to capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc., and that enable the camera and image capture when invoked would be embedded in the media presentation social media sharing, and so on. However, tags embedded in the media presentation that are related to advertisements would not enable the camera when invoked. Various other situations of tag invocation are also possible.

Figure 13:
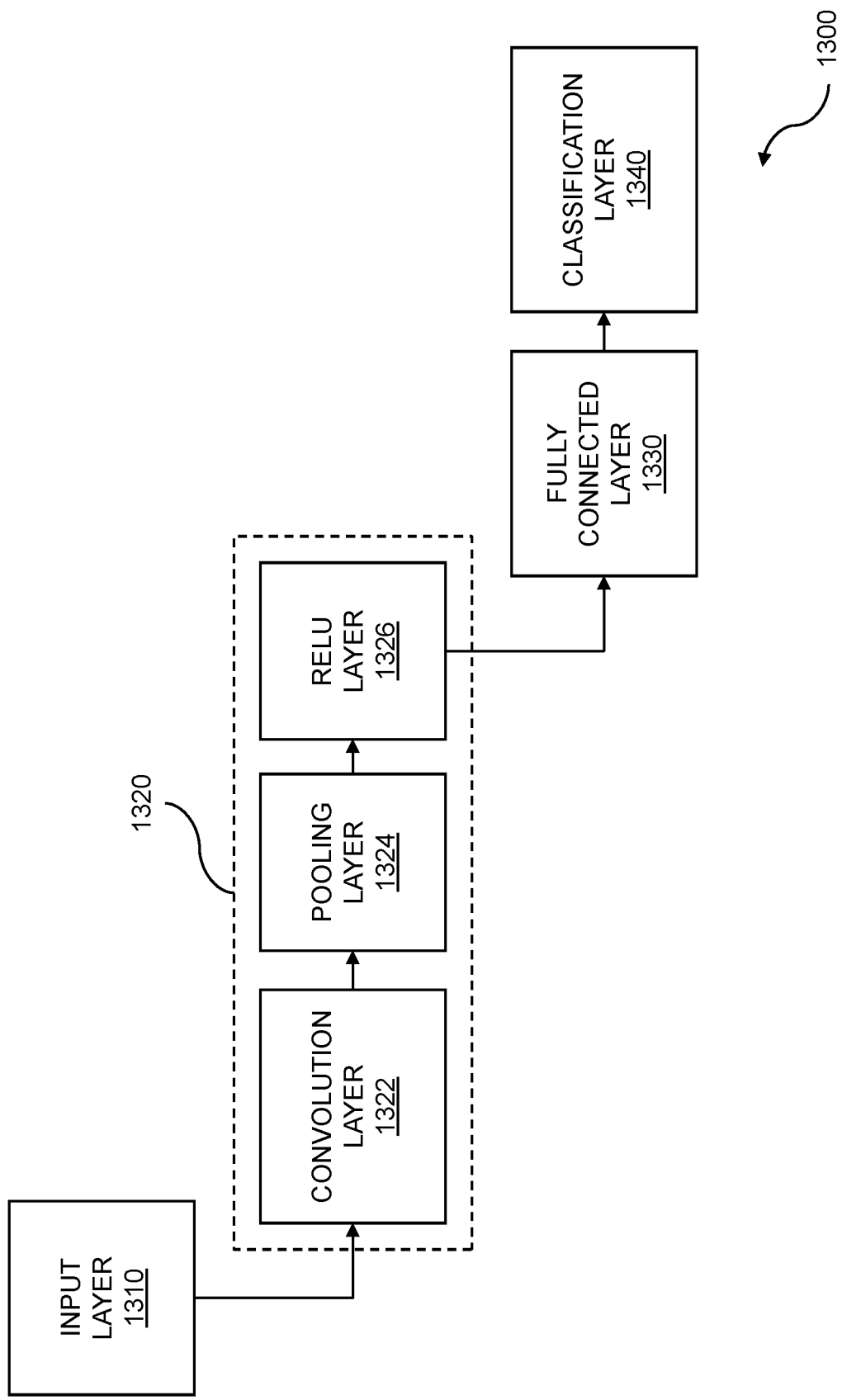
FIG. 13 is an example showing a convolutional neural network (CNN).

FIG. 13 is an example showing a convolutional neural network (CNN). The convolutional neural network can be used for deep learning, where the deep learning can be applied to vehicle manipulation using occupant image analysis. Cognitive state data including facial data is collected on an occupant of a vehicle. A cognitive state profile is learned. Further cognitive state data is captured, and the further data is compared to the cognitive state profile. A second vehicle is manipulated based on the comparison of the further cognitive state data. The convolutional neural network can be applied to such tasks as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, require a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network, which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 13 is an example showing a convolutional neural network 1300. The convolutional neural network can be used for deep learning, where the deep learning can be applied to avatar image animation using translation vectors. The deep learning system can be accomplished using a convolution neural network or other techniques. The deep learning can accomplish facial recognition and analysis tasks. The network includes an input layer 1310. The input layer 1310 receives image data. The image data can be input in a variety of formats, such as JPEG, TIFF, BMP, and GIF. Compressed image formats can be decompressed into arrays of pixels, wherein each pixel can include an RGB tuple. The input layer 1310 can then perform processing such as identifying boundaries of the face, identifying landmarks of the face, extracting features of the face, and/or rotating a face within the plurality of images.

The network includes a collection of intermediate layers 1320. The multilayered analysis engine can include a convolutional neural network. Thus, the intermediate layers can include a convolution layer 1322. The convolution layer 1322 can include multiple sublayers, including hidden layers within it. The output of the convolution layer 1322 feeds into a pooling layer 1324. The pooling layer 1324 performs a data reduction, which makes the overall computation more efficient. Thus, the pooling layer reduces the spatial size of the image representation to reduce the number of parameters and computations in the network. In some embodiments, the pooling layer is implemented using filters of size 2×2, applied with a stride of two samples for every depth slice along both width and height, resulting in a reduction of 75-percent of the downstream node activations. The multi-layered analysis engine can further include a max pooling layer. Thus, in embodiments, the pooling layer 1324 is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1326. The output of the pooling layer 1324 can be input to the RELU layer 1326. In embodiments, the RELU layer implements an activation function such as $f(x)-\max(0,x)$, thus providing an activation with a threshold at zero. In some embodiments, the RELU layer 1326 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1322 and one or more hidden layers, and wherein the multilayered analysis engine can be used for emotional analysis.

The example 1300 includes a fully connected layer 1330. The fully connected layer 1330 processes each pixel/data point from the output of the collection of intermediate layers 1320. The fully connected layer 1330 takes all neurons in the previous layer and connects them to every single neuron it has. The output of the fully connected layer 1330 provides input to a classification layer 1340. The output of the classification layer 1340 provides a facial expression and/or cognitive state as its output. Thus, a multilayered analysis engine such as the one depicted in FIG. 13 processes image data using weights, models the way the human visual cortex performs object recognition and learning, and is effective for analysis of image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and sub-optimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include a person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing the weighting values within the model, algorithm, etc. Positive outcomes may result in increasing the weighting values. Negative outcomes can also be considered, where weighting values may be reduced or otherwise adjusted.

Figure 14:
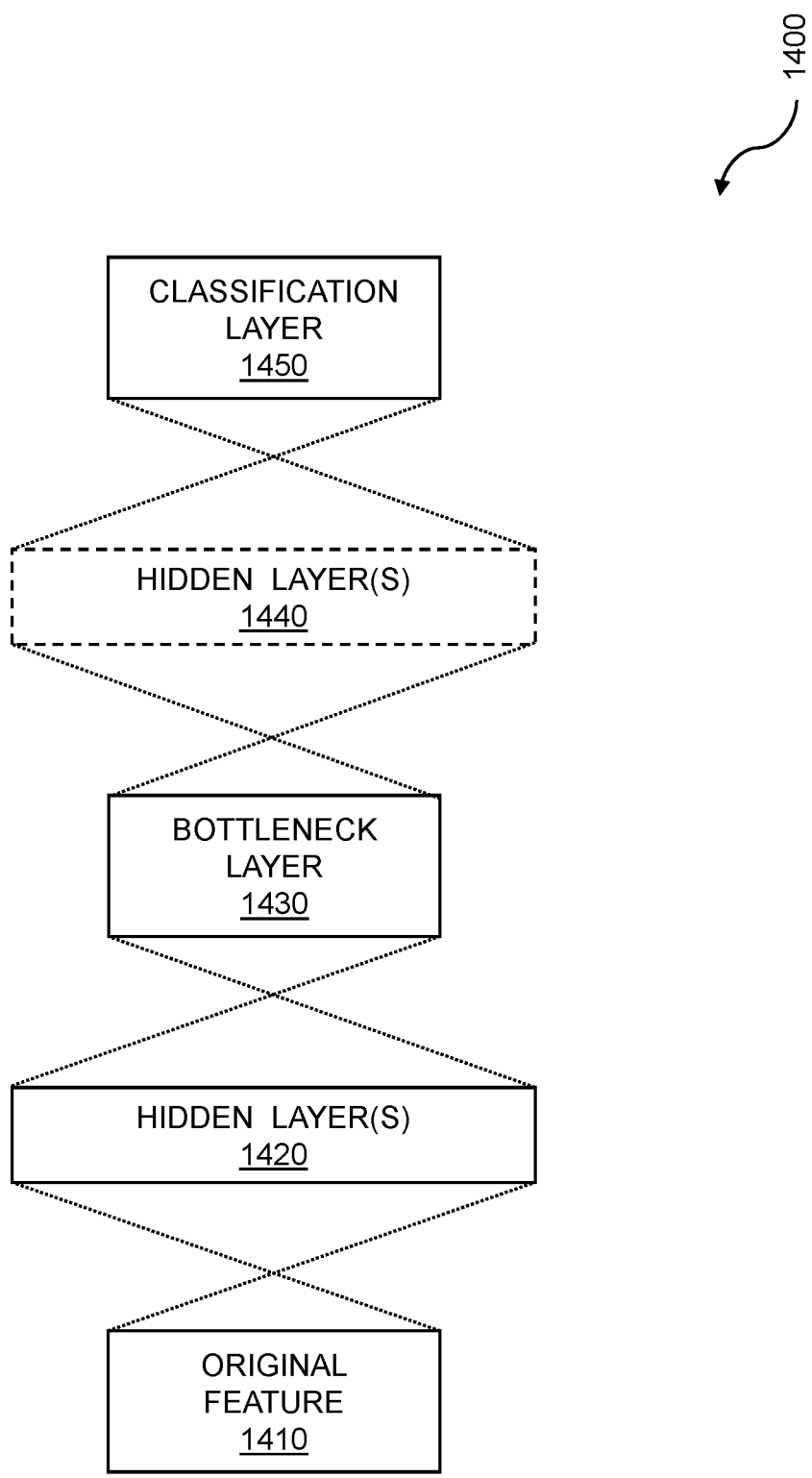
FIG. 14 illustrates a bottleneck layer within a deep learning environment.

FIG. 14 illustrates a bottleneck layer within a deep learning environment. A bottleneck layer can be one of a plurality of layers in a deep neural network. The bottleneck layer can be used for vehicle manipulation using occupant image analysis. A deep neural network can apply classifiers such as image classifiers, audio classifiers, and so on. The classifiers can be learned by analyzing cognitive state data. Cognitive state data on an occupant of a vehicle is collected using a camera, and a cognitive state profile is learned.

Further cognitive state data is captured, and the further cognitive state data is compared with the cognitive state profile. A second vehicle is manipulated based on the comparing of the further cognitive state data.

Layers of a deep neural network can include a bottleneck layer 1400. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1410. A feature such as an image feature can include points, edges, objects, boundaries between and among regions, properties, and so on. The deep neural network can include one or more hidden layers 1420. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1430. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised manner. The supervised technique can include training the deep neural network with a known dataset. The features can be extracted from an autoencoder such as a variational autoencoder, a generative autoencoder, and so on. The deep neural network can include hidden layers 1440. The number of the hidden layers can include zero hidden layers, one hidden layer, a plurality of hidden layers, and so on. The hidden layers following the bottleneck layer can include more nodes than the bottleneck layer. The deep neural network can include a classification layer 1450. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 15:
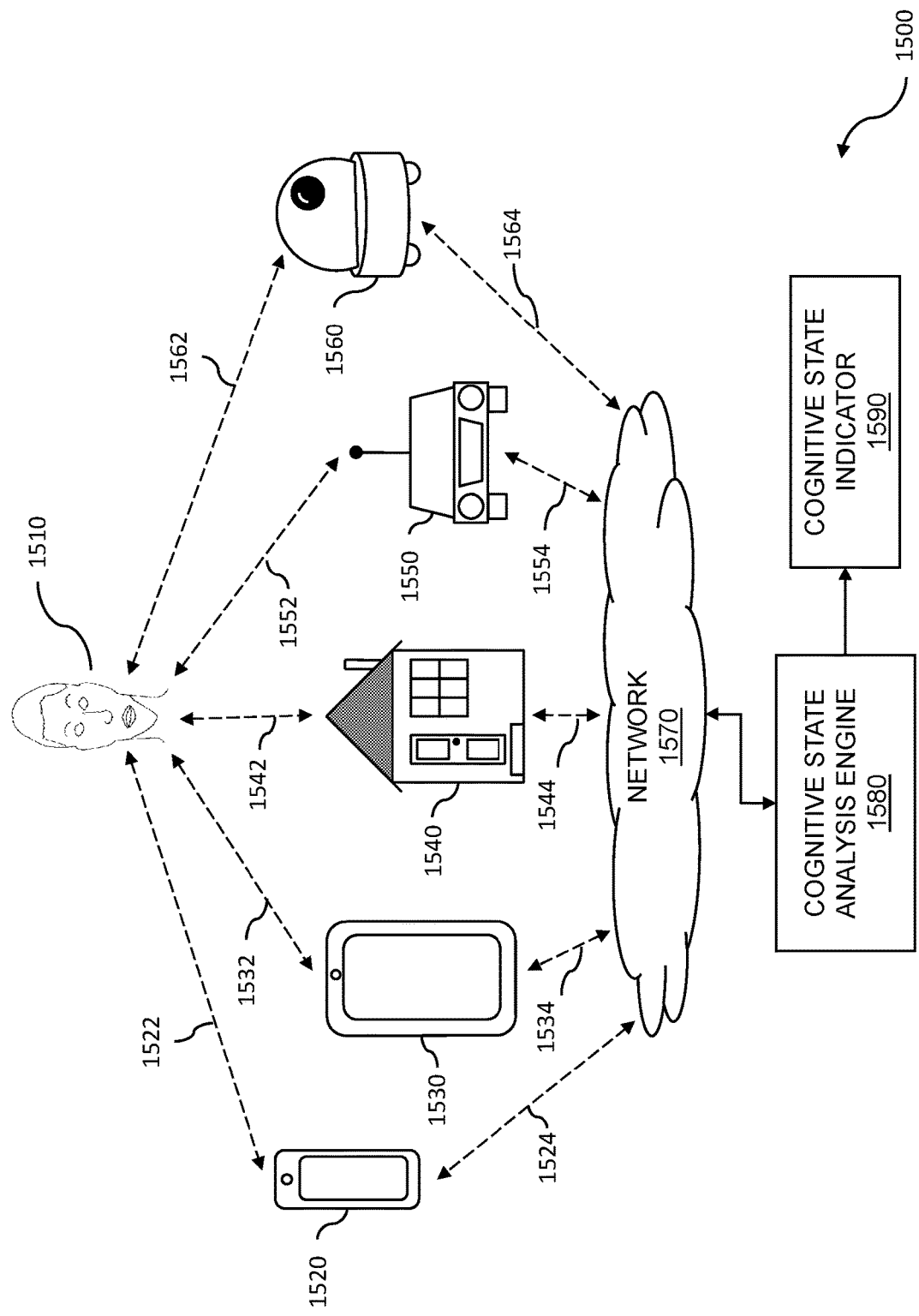
FIG. 15 shows data collection including devices and locations.

FIG. 15 shows data collection including devices and locations 1500. Data, including video data and audio data, can be collected for vehicle manipulation using occupant image analysis. Video data including facial data is collected on a vehicle occupant, and a cognitive state profile is learned. Further cognitive state data is captured and compared with the cognitive state profile. A second vehicle is manipulated based on the comparison of the further cognitive state data. The multiple mobile devices, vehicles, and locations, can be used separately or in combination to collect video data on a user 1510. While one person is shown, the video data can be collected on multiple people. A user 1510 can be observed as she or he is performing a task, experiencing an event, viewing a media presentation, and so on. The user 1510 can be shown one or more media presentations, political presentations, social media, or another form of displayed media. The one or more media presentations can be shown to a plurality of people. The media presentations can be displayed on an electronic display coupled to a client device. The data collected on the user 1510 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1510 can be analyzed and viewed for a variety of purposes including expression analysis, mental state analysis, cognitive state analysis, and so on. The electronic display can be on a smartphone 1520 as shown, a tablet computer 1530, a personal digital assistant, a television, a mobile monitor, or any other type of electronic device. In one embodiment, expression data is collected on a mobile device such as a cell phone or smartphone 1520, a tablet computer 1530, a laptop computer, or a watch. Thus, the multiple sources can include at least one mobile device, such as a smartphone 1520 or a tablet computer 1530, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1510, data can be collected in a house 1540 using a web camera or the like; in a vehicle 1550 using a web camera, client device, etc.; by a social robot 1560; and so on.

As the user 1510 is monitored, the user 1510 might move due to the nature of the task, boredom, discomfort, distractions, or for another reason. As the user moves, the camera with a view of the user's face can be changed. Thus, as an example, if the user 1510 is looking in a first direction, the line of sight 1522 from the smartphone 1520 is able to observe the user's face, but if the user is looking in a second direction, the line of sight 1532 from the tablet computer 1530 is able to observe the user's face. Furthermore, in other embodiments, if the user is looking in a third direction, the line of sight 1542 from a camera in the house 1540 is able to observe the user's face, and if the user is looking in a fourth direction, the line of sight 1552 from the camera in the vehicle 1550 is able to observe the user's face. If the user is looking in a fifth direction, the line of sight 1562 from the social robot 1560 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1510 can also use a wearable device including a camera for gathering contextual information and/or collecting expression data on other users. Because the user 1510 can move her or his head, the facial data can be collected intermittently when she or he is looking in a direction of a camera. In some cases, multiple people can be included in the view from one or more cameras, and some embodiments include filtering out faces of one or more other people to determine whether the user 1510 is looking toward a camera. All or some of the expression data can be continuously or sporadically available from the various devices and other devices.

The captured video data can include cognitive content, such as facial expressions, etc., and can be transferred over a network 1570. The network can include the Internet or other computer network. The smartphone 1520 can share video using a link 1524, the tablet computer 1530 using a link 1534, the house 1540 using a link 1544, the vehicle 1550 using a link 1554, and the social robot 1560 using a link 1564. The links 1524, 1534, 1544, 1554, and 1564 can be wired, wireless, and hybrid links. The captured video data, including facial expressions, can be analyzed on a cognitive state analysis engine 1580, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the cognitive state analysis engine can be processed by a cognitive state indicator 1590. The cognitive state indicator 1590 can indicate cognitive states, mental states, moods, emotions, etc. In embodiments, the cognitive content can include detection of one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 16:
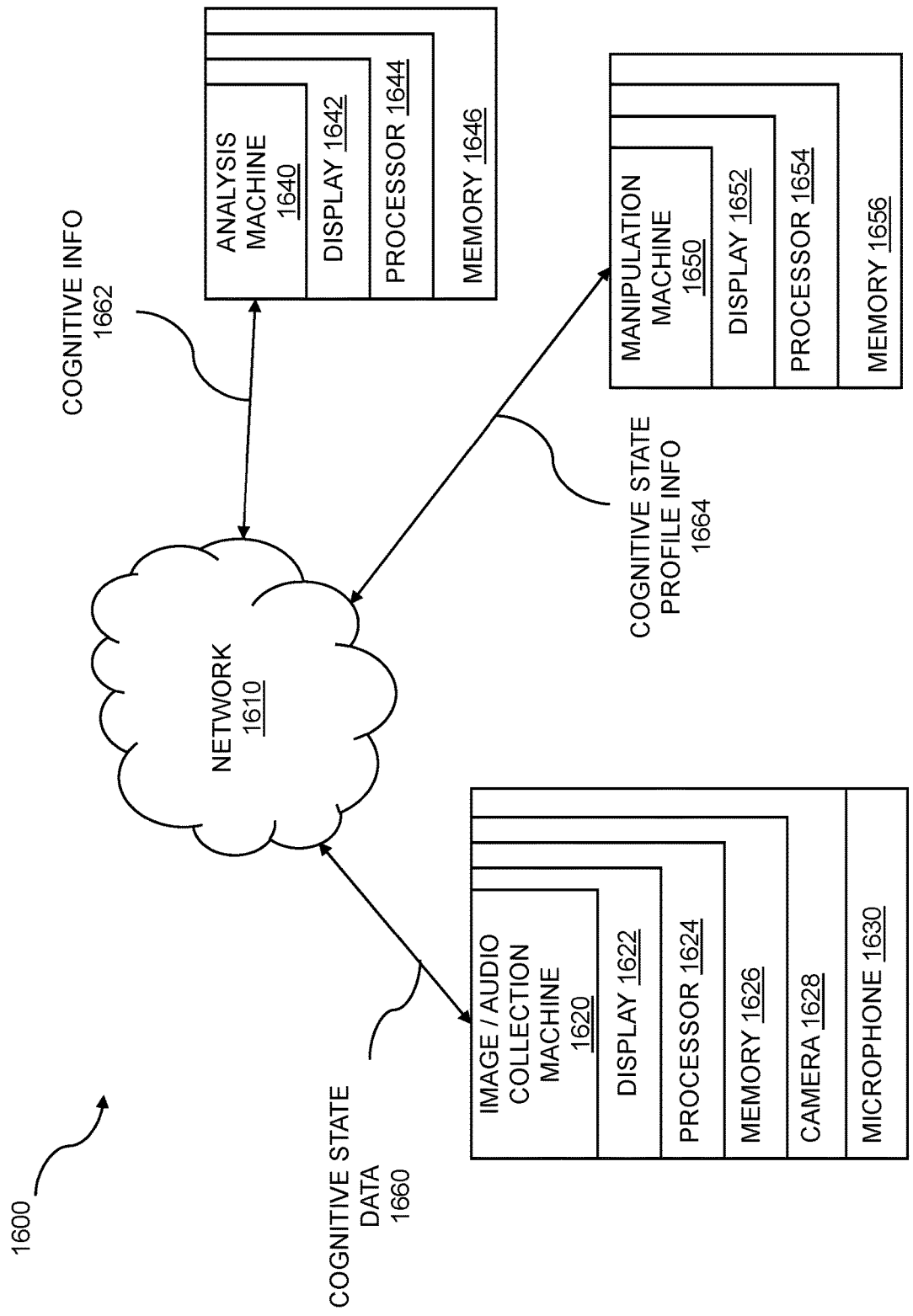
FIG. 16 is a diagram of a system for analyzing web-enabled application traffic states utilizing multiple computers.

FIG. 16 is a system diagram 1600 for vehicle manipulation. The vehicle manipulation can be based on using occupant image analysis. A camera within a vehicle is used for collecting cognitive state data, including facial data, on an occupant of a vehicle. A cognitive state profile is learned, on a first computing device, for the occupant based on the cognitive state data. Further cognitive state data on the occupant is captured, on a second computing device, while the occupant is in a second vehicle. The further cognitive state data is compared, on a third computing device, with the cognitive state profile that was learned for the occupant. The second vehicle is manipulated based on the comparing of the further cognitive state data. The network 1610, Internet, intranet, or another computer network, can be used for communication between and among various machines. An image and audio collection machine 1620 has a memory 1626 which stores instructions and one or more processors 1624 attached to the memory 1626, wherein the one or more processors 1624 can execute instructions. In some embodiments, the image and audio collection machine 1620 includes a camera 1628 and a microphone 1630, although in some embodiments, camera images and microphone audio can be obtained through external means (not shown). The image and audio collection machine 1620 can also have a network connection to carry cognitive state data 1660 and a display 1622 that can present cognitive state data, cognitive state profiles, mental state data, mental state profiles, emotional states, emotional state profiles, and so on. The image and audio collection machine 1620 can collect cognitive state data including facial data, voice data, audio data, etc., from an occupant of a vehicle. In some embodiments, there are multiple image and audio collection machines 1620 that each collect cognitive state data including facial data. Further embodiments include collecting voice data and augmenting the cognitive state data with the voice data. Once the cognitive state data 1660 has been collected, the image and audio collection machine 1620 can upload information to an analysis machine 1640 based on the cognitive state data from the occupant of the vehicle. The image and audio collection machine 1620 can communicate with the analysis machine 1640 over the network 1610, the Internet, some other computer network, or by another method suitable for communication between two machines. In some embodiments, the analysis machine 1640 functionality is embodied in the image and audio collection machine 1620.

The analysis machine 1640 can have a network connection for cognitive states or cognitive state information 1662, a display 1642, a memory 1646 which stores instructions, and one or more processors 1644 attached to the memory 1646, wherein the one or more processors 1644 can execute instructions. The analysis machine 1640 can receive cognitive state information, collected from an occupant of the vehicle, from the image and audio collection machine 1620, and can learn a cognitive state profile for the occupant. The analysis machine 1640 can also compare further cognitive state data with the cognitive state profile while the occupant is in a second vehicle. In some embodiments, the analysis machine 1640 also allows a user to view and evaluate the cognitive state data and cognitive state profiles for the occupant of the vehicle on a display 1642. The analysis machine 1640 can then provide the cognitive state profile information 1664 to the manipulation machine 1650. In some embodiments, the image and audio collection machine 1620 can also function as the manipulation machine 1650.

The manipulation machine 1650 can have a memory 1656 which stores instructions, and one or more processors 1654 attached to the memory 1656, wherein the one or more processors 1654 can execute instructions. The manipulation machine can use a computer network, the Internet, or another computer communication method, to request the cognitive state information 1662 from the analysis machine. The manipulation machine 1650 can receive cognitive state profile information 1664, based on the cognitive state data 1660, from the occupant of the vehicle. The cognitive state information and cognitive state profile information for the occupant can be presented on a display 1652. In some embodiments, the manipulation machine is set up to receive cognitive state data collected from an occupant of the vehicle, in a real-time or near real-time embodiment. In at least one embodiment, a single computer incorporates the image and audio collection machine, the analysis machine, and manipulation machine functionalities.

In embodiments, a computer program product is embodied in a non-transitory computer readable medium for vehicle manipulation, the computer program product comprising code which causes one or more processors to perform operations of: collecting, using a camera within a vehicle, cognitive state data including facial data, on an occupant of a vehicle; learning a cognitive state profile for the occupant based on the cognitive state data; capturing further cognitive state data on the occupant while the occupant is in a second vehicle; comparing the further cognitive state data with the cognitive state profile that was learned for the occupant; and manipulating the second vehicle based on the comparing of the further cognitive state data.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products, and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for vehicle manipulation comprising:
   collecting, using a camera within a vehicle, cognitive state data including facial data, on an occupant of a vehicle;
   learning, on a first computing device, a cognitive state profile for the occupant based on the cognitive state data;
   capturing, on a second computing device, further cognitive state data on the occupant while the occupant is in a second vehicle;
   comparing, on a third computing device, the further cognitive state data with the cognitive state profile that was learned for the occupant; and
   manipulating the second vehicle based on the comparing of the further cognitive state data.

2. The method of claim 1 wherein the cognitive state profile includes information on absolute time.

3. The method of claim 2 wherein the absolute time includes time of day, day of week, day of month, or time of year information.

4. The method of claim 1 further comprising collecting voice data and augmenting the cognitive state data with the voice data.

5. The method of claim 4 wherein the voice data includes audio data.

6. The method of claim 4 further comprising evaluating the voice data for timbre, prosody, vocal register, vocal resonance, pitch, loudness, speech rate, or language content.

7. The method of claim 4 wherein the augmenting is based on lexical analysis of the voice data that looks at sentiment.

8. The method of claim 4 wherein the voice data includes non-speech vocalizations.

9. The method of claim 8 wherein the non-speech vocalizations include grunts, yelps, squeals, snoring, sighs, laughter, filled pauses, unfilled pauses, or yawns.

10. The method of claim 1 wherein the occupant is a passenger within the vehicle.

11. The method of claim 10 wherein the vehicle is an autonomous vehicle.

12. The method of claim 1 wherein the vehicle is a semi-autonomous vehicle.

13. The method of claim 1 further comprising performing facial recognition on the occupant.

14. The method of claim 13 further comprising using the cognitive state profile across a fleet of vehicles.

15. The method of claim 1 wherein the vehicle and the second vehicle are a same vehicle.

16. The method of claim 1 wherein the vehicle and the second vehicle are different vehicles.

17. The method of claim 1 wherein the vehicle and the second vehicle are part of a fleet of vehicles.

18. The method of claim 1 wherein the manipulating includes a locking out operation; recommending a break for the occupant; recommending a different route; recommending how far to drive; responding to traffic; adjusting seats, mirrors, climate control, lighting, music, audio stimuli, interior temperature for the second vehicle; brake activation; or steering control.

19. The method of claim 1 wherein the manipulating is based on a make for the second vehicle, a vehicle class for the second vehicle, tires for the second vehicle, a weather pattern, and a traffic pattern.

20. The method of claim 1 further comprising capturing cognitive state data on a second occupant and manipulating the second vehicle based on the cognitive state data for the occupant and the cognitive state data for the second occupant.

21. The method of claim 1 further comprising comparing the further cognitive state data with additional cognitive state profiles learned from additional occupants of additional vehicles.

22. The method of claim 21 wherein the additional cognitive state profiles are selected based on demographics of the occupant.

23. The method of claim 21 wherein the additional cognitive state profiles are selected based on characteristics of the vehicle of the occupant.

24. The method of claim 21 wherein the additional cognitive state profiles are selected based on a route being travelled.

25. A computer program product embodied in a non-transitory computer readable medium for vehicle manipulation, the computer program product comprising code which causes one or more processors to perform operations of:
   collecting, using a camera within a vehicle, cognitive state data including facial data, on an occupant of a vehicle;
   learning a cognitive state profile for the occupant based on the cognitive state data;
   capturing further cognitive state data on the occupant while the occupant is in a second vehicle;
   comparing the further cognitive state data with the cognitive state profile that was learned for the occupant; and
   manipulating the second vehicle based on the comparing of the further cognitive state data.

26. A computer system for vehicle manipulation comprising:
   a memory which stores instructions;
   one or more processors attached to the memory wherein the one or more processors, when executing the instructions which are stored, are configured to:
      collect, using a camera within a vehicle, cognitive state data including facial data, on an occupant of a vehicle;
      learn a cognitive state profile for the occupant based on the cognitive state data;
      capture further cognitive state data on the occupant while the occupant is in a second vehicle;
      compare the further cognitive state data with the cognitive state profile that was learned for the occupant; and
      manipulate the second vehicle based on the comparing of the further cognitive state data.

* * * * *